United States Patent
Amini et al.

(10) Patent No.: US 11,248,265 B1
(45) Date of Patent: Feb. 15, 2022

(54) SYSTEMS AND PROCESSES FOR DISTINGUISHING PATHOGENIC AND NON-PATHOGENIC SEQUENCES FROM SPECIMENS

(71) Applicant: Clear Labs, Inc., San Carlos, CA (US)

(72) Inventors: Sasan Amini, Redwood City, CA (US); Ramin Khaksar, Redwood City, CA (US); Michael Taylor, Kensington, MD (US); Prasanna Thwar Krishnan, San Jose, CA (US); David Tran, Santa Rosa, CA (US); Shaokang Zhang, Union City, CA (US); Shadi Shokralla, Danville, CA (US); Kyle Rhoden, Omaha, NE (US); Susan Jisoon Lee, South San Francisco, CA (US); Bryan Thomas Barney, San Jose, CA (US); Sima Mortazavi, East Palo Alto, CA (US); Adam Forrest Allred, San Carlos, CA (US); Henrik Gehrmann, Newark, CA (US)

(73) Assignee: CLEAR LABS, INC, San Carlos, CA (US)

( * ) Notice: Subject to any disclaimer, the term of this patent is extended or adjusted under 35 U.S.C. 154(b) by 0 days.

(21) Appl. No.: 17/102,407

(22) Filed: Nov. 23, 2020

Related U.S. Application Data

(60) Provisional application No. 63/116,089, filed on Nov. 19, 2020.

(51) Int. Cl.
*C12Q 1/6869* (2018.01)
*C12Q 1/70* (2006.01)

(52) U.S. Cl.
CPC ............ *C12Q 1/6869* (2013.01); *C12Q 1/70* (2013.01); *C12Q 2535/122* (2013.01); *C12Q 2563/185* (2013.01)

(58) Field of Classification Search
None
See application file for complete search history.

(56) References Cited

U.S. PATENT DOCUMENTS

| | | |
|---|---|---|
| 10,101,328 B1 | 10/2018 | Amini et al. |
| 10,159,971 B2 | 12/2018 | Amini et al. |
| 10,246,704 B1 | 4/2019 | Amini et al. |
| 10,597,714 B2 | 3/2020 | Amini et al. |
| 10,676,794 B2 | 6/2020 | Amini et al. |
| 2001/0034020 A1* | 10/2001 | Zimmermann .. C12Q 2521/301 435/5 |
| 2020/0102608 A1 | 4/2020 | Crawford et al. |

FOREIGN PATENT DOCUMENTS

| | | |
|---|---|---|
| WO | 2016179190 A1 | 11/2016 |
| WO | 2018195483 A1 | 10/2018 |
| WO | 2019090251 A3 | 5/2019 |
| WO | 2019133756 A1 | 7/2019 |
| WO | 2020242985 A1 | 12/2020 |

OTHER PUBLICATIONS

Rockey et al. UV Disinfection of Human Norovirus: Evaluating Infectivity Using a Genome-Wide PCR-Based Approach. Environmental Science & Technology 54:2851-2858, Jan. 24, 2020 (Year: 2020).*
Rockey Supporting Information [online] Jan. 24, 2020 [retrieved on Mar. 20, 2021], retrieved from: http://pubs.acs.org/doi/suppl/10.1021/acs.est.9b05747/suppl_file/es9b05747_si_001.pdf (Year: 2020).*
Pecson et al. Framework for Using Quantitative PCR as a Nonculture Based Method to Estimate Virus Infectivity. Environmental Science & Technology 45:2257-2263 (Year: 2011).*
Player et al. Comparison of the performance of an amplicon sequencing assay based on Oxford Nanopore technology to real-time PCR assays for detecting bacterial biodefense pathogens. BMC Genomics 21:166 (21 pages) (Year: 2020).*
Sohn et al. Assessing Viral Shedding and Infectivity of Asymptomatic or Mildly Symptomatic Patients with COVID-19 in a Later Phase. J. Clin. Med. 9:2924, Sep. 10, 2020 (9 pages) (Year: 2020).*
Jousimies-Somer et al. Comparison of the Nasal Bacterial Floras in Two Groups of Healthy Subjects and in Patients with Acute Maxillary Sinusitis. J. Clin. Microbiol. 27(12):2736-2743 (Year: 1989).*
Huang et al. Detection of infectious dengue virus by selective real-time quantitative polymerase chain reaction. Virologica Sinica 31(4):342-345 (Year: 2016).*
Aytay et al. Development of a sensitive PCR inhibition method to demonstrate HBV nucleic acid inactivation. Transfusion 44:476-484. (Year: 2004).*
Banihashemi et al. Long-amplicon propidium monoazide-PCR enumeration assay to detect viable Campylobacter and *Salmonella*. Journal of Applied Microbiology 113:863-873. (Year: 2012).*
Bhattacharya et al. Use of reverse transcription and PCR to discriminate between infectious and non-infectious hepatitis A virus. Journal of Virological Methods 116:181-187. (Year: 2004).*

(Continued)

*Primary Examiner* — Samuel C Woolwine
(74) *Attorney, Agent, or Firm* — Naira Simmons; FisherBroyles, LLP

(57) ABSTRACT

Provided herein are fully-automated next-generation sequencing platforms and processes for detection of a target specimen (e.g., SARS-CoV-2) and for distinguishing infectious from non-infectious signals from the specimen. An analysis can provide simultaneous diagnosis and genomic surveillance of a multitude of distinct specimens in a sample information. The analysis can comprise distinguishing between infectious versus infectious specimens and provide a recommendation as to how infectious the sample can be. The information can be used to better inform the status of a subject or a location with regards to infectivity from the specimen.

26 Claims, 25 Drawing Sheets

(56) References Cited

OTHER PUBLICATIONS

Coudray-Meunier et al. Discrimination of infectious hepatitis A virus and rotavirus by combining dyes and surfactants with RT-qPCR. BMC Microbiology 13:216 (16 pages). (Year: 2013).*
Fittipaldi et al. Discrimination of infectious bacteriophage T4 virus by propidium monoazide real-time PCR. Journal of Virological Methods 168:228-232. (Year: 2010).*
Fongaro et al. Propidium monoazide coupled with PCR predicts infectivity of enteric viruses in swine manure and biofertilized soil. Food Environ Virol 8:79-85. (Year: 2016).*
Ho et al. Long amplicon (LA)-qPCR for the discrimination of infectious and noninfectious phix174 bacteriophages after UV inactivation. Water Research 103:141-148. (Year: 2016).*
Ji et al. Rapid and accurate sequencing of enterovirus genomes using MinION Nanopore Sequencer. Biomed Environ Sci 30(10): 718-726. (Year: 2017).*
Karim et al. Propidium monoazide reverse transcriptase PCR and RT-qPCR for detecting infectious enterovirus and norovirus. Journal of Virological Methods 219:51-61. (Year: 2015).*
Lee, S. Testing for SARS-CoV-2 in cellular components by routine nested RT-PCR followed by DNA sequencing. International Journal of Geriatrics and Rehabilitation 2(1):69-96. (Year: 2020).*
Leifels et al. Use of ethidium monoazide and propidium monoazide to determine viral infectivity upon inactivation by heat, UV-exposure and chlorine. International Journal of Hygiene and Environmental Health 218:686-693. (Year: 2015).*
Moore et al. Amplicon based MinION sequencing of SARS-CoV-2 and metagenomic characterisation of nasopharyngeal swabs from patients with COVID-19, [online] Mar. 8, 2020 [retrieved on Sep. 22, 2021] retrieved from: https://www.medrxiv.org/content/10.1101/2020.03.05.20032011v1 (Year: 2020).*
Moreno et al. Application of viability PCR to discriminate the infectivity of hepatitis A virus in food samples. International Journal of Food Microbiology 201:1-6. (Year: 2015).*
Nakaya et al. Quick assessment of influenza A virus infectivity with a long-range reverse-transcription quantitative polymerase chain reaction assay. BMC Infectious Diseases 20:585 (10 pages). (Year: 2020).*
Oristo et al. Performance of pre-RT-qPCR treatments to discriminate infectious human rotaviruses and noroviruses from heat-inactivated viruses: applications of PMA/PMAxx, benzonase and RNase. Journal of Applied Microbiology 124:1008-1016. (Year: 2018).*
Parshionikar et al. Use of propidium monoazide in reverse transcriptase PCR to distinguish between infectious and noninfectious enteric viruses in water samples. Applied and Environmental Microbiology 76:4318-4326. (Year: 2010).*
Randazzo et al. Evaluation of viability PCR performance for assessing norovirus infectivity in fresh-cut vegetables and irrigation water. International Journal of Food Microbiolgy 229:1-6. (Year: 2016).*
Rodriguez et al. Application of PCR-based methods to assess the infectivity of enteric viruses in environmental samples. Applied and Environmental Microbiology 75:297-307. (Year: 2009).*
Sawyer et al. Inactivation of parvovirus B19 in human platelet concentrates by treatment with amotosalen and ultraviolet A illumination. Transfusion 47:1062-1070. (Year: 2007).*
Tsujikawa et al. Caution in evaluation of removal of virus by filtration: Misinterpretation due to detection of viral genome fragments by PCR. Journal of Virological Methods 178:39-43. (Year: 2011).*
Unnithan et al. Enzymatic Pre-treatment of Wastewater to Minimize Recovery by Reverse Transcriptase PCR of RNA from Inactive Bacteriophages. Curr Microbiol 71:49-53. (Year: 2015).*
Quick et al. Multiplex PCR method for MinION and Illumina sequencing of Zika and other virus genomes directly from clinical samples. Nature Protocols 12(6):1261-1276. (Year: 2017).*
"AMP Cautions Against Using Cycle Threshold Values for PCR SARS-CoV-2 Tests in Clinical Practice", 360Dx, Apr. 21, 2021.
Cohen et al., "False positives in reverse transcription PCR testing for SARS-CoV-2", medRxiv, May 1, 2020, https://doi.org/10.1.101/2020.04.26.20080911.
"IDSA and AMP joint statement on the use of SARS-CoV-2 PCR cycle threshold (Ct) values for clinical decision-making", IDSA & AMP, Mar. 12, 2021.

\* cited by examiner

1000 copies/ul

| Size [bp] | Conc. [ng/μl] | Molarity [nmol/l] |
|---|---|---|
| 15 | 4.2 | 424.2 |
| 114 | 3.54 | 47 |
| 333 | 7.43 | 33.8 |
| 556 | 3.19 | 8.7 |
| 831 | 5.64 | 10.3 |
| 1,500 | 2.1 | 2.1 |

100 copies/ul

| Size [bp] | Conc. [ng/μl] | Molarity [nmol/l] |
|---|---|---|
| 15 | 4.2 | 424.2 |
| 114 | 1.85 | 24.7 |
| 332 | 3.83 | 17.5 |
| 551 | 2.51 | 6.9 |
| 830 | 2.21 | 4 |
| 1,500 | 2.1 | 2.1 |

5 copies/ul

| Size [bp] | Conc. [ng/μl] | Molarity [nmol/l] |
|---|---|---|
| 15 | 4.2 | 424.2 |
| 113 | 0.87 | 11.7 |
| 330 | 0.74 | 3.4 |
| 548 | 0.89 | 2.5 |
| 834 | 2.26 | 4.1 |
| 1,500 | 2.1 | 2.1 |

2 copies/ul

| Size [bp] | Conc. [ng/µl] | Molarity [nmol/l] |
|---|---|---|
| 15 | 4.2 | 424.2 |
| 114 | 0.67 | 9 |
| 332 | 0.69 | 3.1 |
| 551 | 1.19 | 3.3 |
| 830 | 1.35 | 2.5 |
| 1,500 | 2.1 | 2.1 |

1x

| Size [bp] | Conc. [ng/µl] | Molarity [nmol/l] |
|---|---|---|
| 15 | 4.2 | 424.2 |
| 114 | 2.81 | 37.3 |
| 332 | 4.5 | 20.6 |
| 554 | 6.32 | 17.3 |
| 819 | 10.69 | 19.8 |
| 1,500 | 2.1 | 2.1 |

| Size [bp] | Conc. [ng/μl] | Molarity [nmol/l] |
|---|---|---|
| 15 | 4.2 | 424.2 |
| 114 | 3.55 | 47 |
| 331 | 4.43 | 20.3 |
| 553 | 4.31 | 11.8 |
| 812 | 5.62 | 10.5 |
| 1,500 | 2.1 | 2.1 |

10x

| Size [bp] | Conc. [ng/μl] | Molarity [nmol/l] |
|---|---|---|
| 15 | 4.2 | 424.2 |
| 114 | 2.14 | 28.4 |
| 332 | 2.9 | 13.3 |
| 554 | 3.63 | 9.9 |
| 813 | 2.13 | 4 |
| 1,500 | 2.1 | 2.1 |

300x

| Size [bp] | Conc. [ng/μl] | Molarity [nmol/l] |
|---|---|---|
| 15 | 4.2 | 424.2 |
| 115 | 2.05 | 27.1 |
| 331 | 3.7 | 16.9 |
| 552 | 1.38 | 3.8 |
| 812 | 1.78 | 3.3 |
| 1,500 | 2.1 | 2.1 |

900x

| Size [bp] | Conc. [ng/μl] | Molarity [nmol/l] |
|---|---|---|
| 15 | 4.2 | 424.2 |
| 114 | 1.63 | 21.6 |
| 331 | 1.2 | 5.5 |
| 551 | 0.7 | 1.9 |
| 812 | 0.8 | 1.5 |
| 1,500 | 2.1 | 2.1 |

1200x

| Size [bp] | Conc. [ng/µl] | Molarity [nmol/l] |
|---|---|---|
| 15 | 4.2 | 424.2 |
| 114 | 1.94 | 25.7 |
| 330 | 3.29 | 15.1 |
| 552 | 0.53 | 1.5 |
| 809 | 0.6 | 1.1 |
| 1,500 | 2.1 | 2.1 |

| Rack | Position | Sample ID | Results | *Subtype | *Clade (Gisaid) | *Mutation | *For Research Use Only |
|---|---|---|---|---|---|---|---|
| 1 | A01 | 19327 | ⊘ SARS-CoV-2 Detected | L type 4 | GH | RdRp P323L, Spike D614G | |
| 1 | B01 | 23547 | ⊘ SARS-CoV-2 Detected | L type 4 | GH | RdRp P323L, Spike D614G | |
| 1 | C01 | 34189 | ⊘ SARS-CoV-2 Detected | L type 5 | G | RdRp P323L, Spike D614G | |
| 1 | D01 | 41714 | ⊘ SARS-CoV-2 Detected | L type 4 | GH | RdRp P323L, Spike D614G | |

FIG. 5

- Person 1 in SF infected first
- Person 1 travels to LA for family event and infects Person 2
- Person 2 goes back to San Diego and infects a co-worker (Person 3)
- Person 3 infects Person 4 in Escondido through local community transmission
- Person 4 infects Person 5 when he goes back to work in Fresno
- Person 5 works in a food plant in Fresno and leads to an outbreak

SYSTEMS AND PROCESSES FOR DISTINGUISHING PATHOGENIC AND NON-PATHOGENIC SEQUENCES FROM SPECIMENS

BACKGROUND

Illnesses caused by microorganism continue to burden populations around the world. Both naturally occurring, and intentionally introduced, pathogenic microorganisms hold increasing potential to cause disease, disability, and death. And beyond disease itself, the ability of infectious agents to destabilize populations, economies, and governments is fast underscoring a need for improved systems for proper prevention and control of infectious microorganisms. There is an unprecedented need for systems and methods that can improve our ability to detect, prevent, and control emerging and resurging microorganism outbreaks.

SUMMARY

Disclosed herein is a processes for distinguishing infectious from non-infectious specimens in a sample, the process comprising: (a) receiving the sample, wherein the sample comprises a plurality of nucleic acids; (b) preparing a nucleic acid library by synthesizing a strand of complementary deoxyribonucleic acid from one or more nucleic acids in the plurality of nucleic acids; (c) amplifying one or more target nucleic acid sequences from the library of step (b) for no more than 40 cycles to generate amplicons of the target nucleic acid(s); (d) sequencing the amplicons of the target nucleic acids from step (c), wherein detection of two or more amplicons of the target nucleic acid of a length greater than 500 bases distinguishes infectious from non-infectious specimens in the sample. In some instances, detection of 2, 3, 4, 5, 6, 7, 8, 9, 10, or more amplicons of the target nucleic acid indicates a viability of a microorganism in the specimen. In preferred embodiments, the length of the target nucleic acid is a proxy of an integrity of the microorganism in the specimen, and an amplicon size detected in (d) greater than 600 base pairs, greater than 650 base pairs, or greater than 700 base pairs indicates that the microorganism is likely intact. In some instances, the amplifying of the target nucleic acid sequence in step (c) comprises using a multiplex set of primers configured to amplify greater than 1%, greater than 5%, greater than 10%, or greater than 20% of a genome encoding the target nucleic acid sequence. In most preferred embodiments, the sensitivity of the assay for the target nucleic acid is two copies of the target nucleic acid per microliter and the accuracy of the assay for the target nucleic acid is higher than 99% as compared to the accuracy of a PCR assay. In some instances the sequencing is sequencing-by-synthesis. In other instances, the sequencing comprises contacting the amplicons with a transmembrane pore such that at least one strand of the amplicons of the target nucleic acid moves through the pore and taking one or more measurements as at least one strand of the amplicon of the target nucleic acid moves through the pore wherein at least one measurement is indicative of a length of the amplicon of the target nucleic acid generated in (c). In such instances, the taking of the one or more measurements detects a direct signal from the at least one strand of the amplicon, a signal that may arise from sub-genomic RNA (sgRNA), genomic RNA (gRNA), or a plasmid. In specific embodiments, the taking of the one or more measurements does not require a fluorescent dye detection moiety. In some instances, the specimen is treated with a reagent that binds and sequesters cell free nucleic acids prior to preparing the library of step (b) and the reagent can be a photo-sensitive dye. In most cases, the plurality of nucleic acids comprise a mixture of viral nucleic acids, mammalian nucleic acids, and bacterial nucleic acids. In some instances, at least one target nucleic acid is selected from the group consisting of SARS-CoV-2, influenza A, influenza B, Human Respiratory Syncytial Virus (RSV), adenovirus, coronavirus 229E, coronavirus HKU1, coronavirus NL63, human metapneumovirus, human rhinovirus/enterovirus, parainfluenza virus 1, parainfluenza virus 2, parainfluenza virus 3, parainfluenza virus 4, *Bordetella parapertussis, Bordetella pertussis, Chlamydophila pneumoniae, Mycoplasma pneumoniae*. In some instances, at least one target nucleic acid is from a bacterium from the *Escherichia* genus, a bacterium from the *Listeria* genus, a bacterium from the *Salmonella* genus, and a bacterium from the *Campylobacter* genus.

Also disclosed herein is a process for tracking an infectious disease in a population by geotagging comprising: (a) receiving a sample, wherein the sample comprises a plurality of nucleic acids and adding a geotag to the sample by providing geographic position information of the sample to a server by a computer so that the server creates a location based geotag based on the geographic position information of the sample; (b) sequencing the plurality of nucleic acids in the sample and creating sequencing digital data having one or more nucleic acid digital sequences derived from a microorganism in the sample; (c) transmitting the sequencing digital data to the server; (d) associating the geographic position information of the sample with the sequencing digital data transmitted to the server; and (e) tracking the infectious disease by associating the one or more nucleic acid sequences derived from the microorganism with the geographic position information of the sample. The process may be repeated with a second sample, or with another suitable number of samples required to track the infectious disease. In preferred embodiments, a report disclosing a geotagged location of the microorganism is delivered to a third-party. The report can be further utilized for contact tracing of individuals in the population that can be associated with the geographic position information of the sample. In some instances, at least one target nucleic acid is selected from the group consisting of SARS-CoV-2, influenza A, influenza B, Human Respiratory Syncytial Virus (RSV), adenovirus, coronavirus 229E, coronavirus HKU1, coronavirus NL63, human metapneumovirus, human rhinovirus/enterovirus, parainfluenza virus 1, parainfluenza virus 2, parainfluenza virus 3, parainfluenza virus 4, *Bordetella parapertussis, Bordetella pertussis, Chlamydophila pneumoniae, Mycoplasma pneumoniae*. In some instances, at least one target nucleic acid is from a bacterium from the *Escherichia* genus, a bacterium from the *Listeria* genus, a bacterium from the *Salmonella* genus, and a bacterium from the *Campylobacter* genus. In other instances, the infectious disease is a sexually transmitted disease, such as HIV. In some instances, the microorganism is antibiotic resistant. The sequencing of the plurality of nucleic acids can be performed in a fully automated platform, such as a platform that comprises a module for preparation of a library from the plurality of nucleic acids from the sample. The library preparation module may be fully equipped to synthesize complementary deoxyribonucleic acid (cDNA) from the plurality of nucleic acids; amplify one or more target sequences from the infections disease being tracked; index the one or more amplified target sequences; and clean up the indexed amplified target sequences in a fully automated fashion. In some cases, nucleic acids derived from the specimen are sequenced by pore sequencing and the pore sequencing chamber takes one or more measurements of the cleaned up indexed amplified target sequences and transmits the data to a server thereby creating pore sequencing digital data. In some instances, the process may track two or more, three or more, or four or more infectious diseases in the population. In most preferred embodiments, the process tracks a plurality of genomic variants of the microorganism by associating one or more nucleic acid sequences derived from the microorganism with the geographic position information of the sample. In some cases, at least one genomic variant is infectious. In other cases, at least one genomic variant is antibiotic resistant. In some instances, a similarity between each genomic variant in the plurality of genomic variants identifies the geographic position of infectious clusters.

In some aspects, disclosed herein are processes from analyzing samples from a subject or samples derived from distinct locations. When derived from a subject the sample can be a nasal swab, a blood sample, a plasma sample, a saliva sample, or a stool sample. When derived from a location the sample can be from a food processing facility, a healthcare facility, a learning center (such as a school, a daycares, tutoring center, or the like), a penitentiary, a commuter station (such as an airport, a train station, a bus station, or the like), an entertainment center (such as a movie theater), or a place of worship. In specific embodiments the location is a sewage water stream and the processes of the disclosure are applied to monitor the overall prevalence of a microorganism in a population. In some cases, a barcode is added to the plurality of nucleotides in the sample for geotracking of the sample. In some instances, the sample is from a sub-location within the location, such as a room or an area within the location. In other instances the sub-location can be a machine, a portal entry, or an equipment within the location. In other instances, the location can be a sewage water stream.

Also disclosed herein are systems for generating and displaying a graphical user interface for high volume data analytics from fully-automated, next-generation sequencing platforms used for simultaneous diagnosis and genomic surveillance of a multitude of microorganisms. The systems and processes disclosed herein provide for a complex multivariate analysis of nucleic acid sequencing data, which categorizes microorganisms as virulent or non-virulent based on their nucleic acid integrity. In some aspects, provided herein are systems and methods that allow the quantitation of disease causing microorganism in a sample, for example, by providing an estimate of a viral load or viral titer in a sample.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 2A illustrate the output of the standard reference, the "ladder. " FIG. 2B illustrate the output of the negative control, "blank. " FIG. 2C-2I illustrate detection of as little as 1.1 nmol/l of the target nucleic acid in a specimen (FIG. 2C=1× dilution; FIG. 2D=10× dilution; FIG. 2E=100× dilution; FIG. 2F=300× dilution; FIG. 2G=900× dilution; and FIG. 1I=1200× dilution).

FIG. 4F illustrate the output of the negative control.

FIG. 5 (FIG. 5) illustrates a graphical user interface reporting subtype, clade, and variants detected by a process of the disclosure.

DETAILED DESCRIPTIONS

Figure 1A:
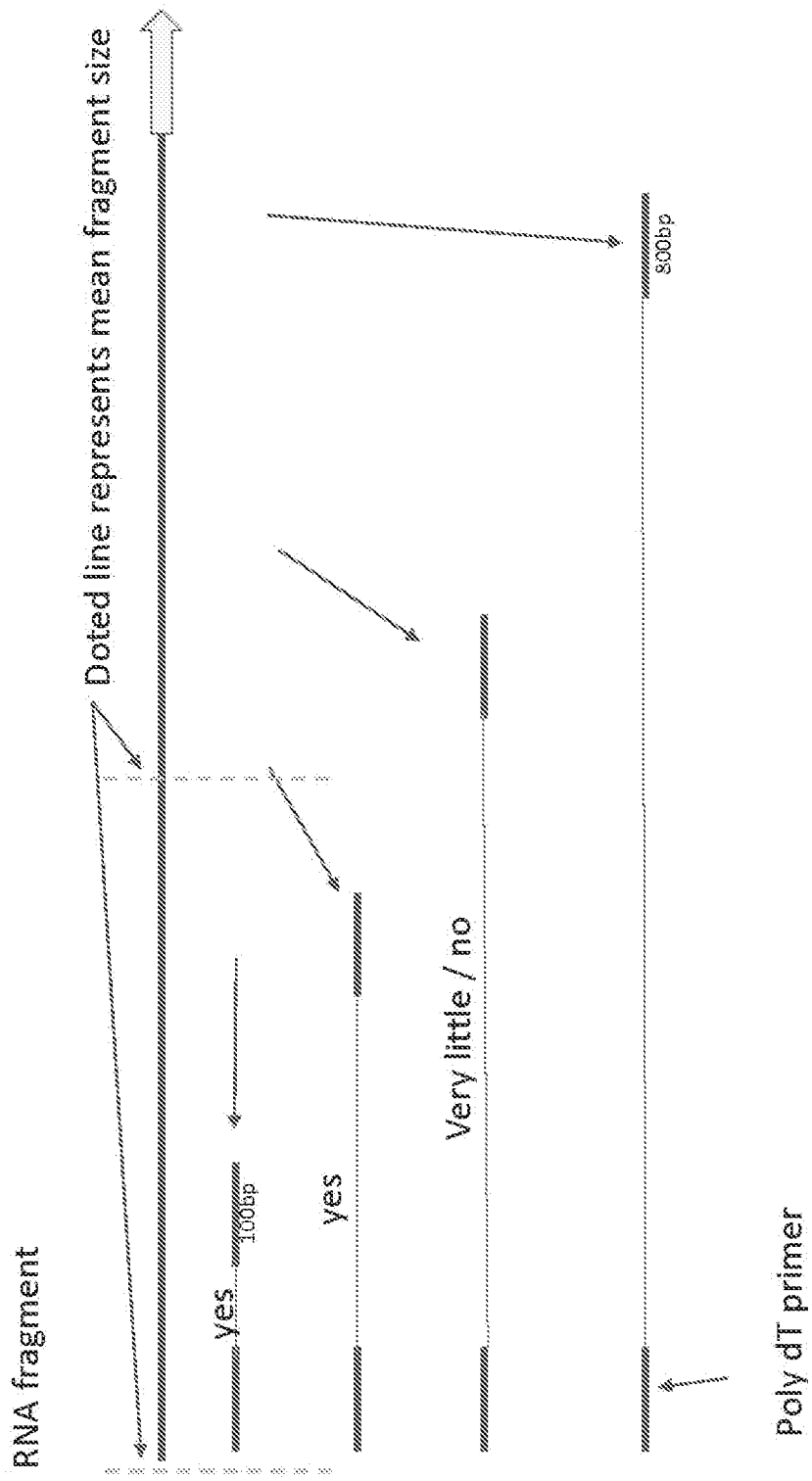
FIG. 1A (FIG. 1A) is a diagram illustrating that specimens with full length RNA should have amplicons for all fragment sizes being amplified, whereas specimens with high fragmentation only generate amplicons for the shorter fragments.

RT-PCR is a widely used testing method for infectious microorganisms across the globe, including SARS-CoV-2. The detection principle of RT-PCR is based on detecting a threshold amount of a target sequence amplified with select primers. Millions of test results across diverse patient groups suggest that SARS-CoV-2 viral loads, measured as Ct values, range from 12 to 40 (8-log range). However, the limitations of the RT-PCR methodology have been significantly exposed as RT-PCR appears to continue identifying presence of SARS-CoV-2 in patients 2-3 months after the initial onset of symptoms and even after their original symptoms have subsided. In some cases, these patients are being classified as having a new COVID-19 infection.

Additional studies have also demonstrated that, in some instances, a positive RT-PCR identification of SARS-CoV-2 in samples with high Ct values (24-30 and above) can be erroneous, and these patients are not infectious. Generally, although RT-PCR methods have been designed to provide the highest analytical sensitivity for detecting SARS-CoV-2, it is unclear how many of these results are "false positives", and what is the positive predictive value of these tests. Also, as each of the RT-PCR tests target different small regions of the viral genome, the Ct values themselves can significantly vary between RT-PCR tests that use distinct primers for amplifying different regions of the same target microorganism (e.g., SARS-CoV-2). Thus, a definitive threshold cannot be set for infectivity. To address these issues, we have developed the first automated targeted long amplicon NGS-based platform. The platform of the disclosure received Clear Dx™, received FDA EUA approval on Sep. 23, 2020 for COVID-19 diagnostics. Since then, the platform of the disclosure has been deployed to public health labs across the United States. The platform may be used in multiple jurisdictions.

One advantage of the platform of the disclosure over state-of-art diagnostic methodologies for microorganism detection—namely RT-PCR—is that the platforms disclosed herein consider significantly longer amplicons and take into account measurements of regions across the entire virus genome. Unexpectedly, we discovered that the systems and processes of the disclosure can not only detect the presence of SARS-CoV-2 RNA, by itself or combined with other microorganism(s), but it can also resolve whether the RNA detected was derived from an infectious source or if was derived from a non-infectious source. As many states and businesses are preparing to reopen fully and operate as normal, knowing whether an asymptomatic individual has an infectious SARS-CoV-2 virus would be tremendously useful to accurately characterize the pandemic and develop effective quarantining and social distancing policies from a public health perspective. The same platform and methodology can be used for the simultaneous monitoring of several other microorganisms.

Provided herein are systems and processes for distinguishing infectious from non-infectious specimens in a sample. In preferred embodiments, the process comprises (a) receiving the sample, wherein the sample comprises a plurality of nucleic acids; (b) preparing a nucleic acid library by synthesizing a strand of complementary deoxyribonucleic acid from one or more nucleic acids in the plurality of nucleic acids; (c) amplifying one or more target nucleic acid sequences from the library of step (b) for no more than 40 cycles to generate amplicons of the target nucleic acid(s); (d) sequencing the amplicons of the target nucleic acids from step (c), wherein detection of two or more amplicons of the target nucleic acid of a length greater than 500 bases distinguishes infectious from non-infectious specimens in the sample.

The process of the disclosure offers multiple technical advantages over the state of art for detection of nucleic acids from a specimen. For instance, the art describes three types of diagnostic methods currently available for COVID-19, and these include a molecular diagnostic method (real-time polymerase chain reaction, RT-PCR), a culture method, and an antigen-antibody test method. The RT-PCR-based tests for COVID-19 are of two types: pancoronavirus RT-PCR and real-time reverse transcription polymerase chain reaction (rRT-PCR). Currently, rRT-PCR is the most widely used diagnostic method for COVID-19. To understand the principle of the assay and the choice of primer sets used, some basic knowledge of COVID-19 biology is necessary. The SARS-CoV-2 genome encodes four structural proteins. The spike surface glycoprotein (S) mediates specific binding to the host cell receptors, the nucleocapsid (N) protein binds to the coronavirus RNA genome to make the nucleocapsid, the membrane (M) protein is the main structural protein that connects between the membrane and the capsid, and the small envelope (E) protein which is involved in the assembly and budding process of the coronavirus. Among them, the genes for the N and E proteins are typically the sole regions used as the targets for amplification in the rRT-PCR assay, and their presence is detected by accumulation of a fluorescent signal. The process of the disclosure obtains a direct signal from a sequence, one that is not dependent on fluorescence from PCR. The processes of the disclosure can readily sequence a minimum of one target nucleic acid sequence, such as the S, N, M, or E region, but it can readily include multiple target regions from all of these sequences or from a select few. Further, the methods of the disclosure can categorize a length of the amplicons, and detection of two or more amplicons of the target nucleic acid of a length greater than 500, a length greater than 600, a length greater than 650, a length greater than 700, a length greater than 750, a length greater than 800, a length greater than 850 bases or base pairs (depending on the sequencing platform used for detection), or another longer suitable length longer than 500 bases or base pairs can distinguish infectious from non-infectious specimens in the sample.

The processes disclosed herein can detect a nucleic acid from a target specimen with high sensitivity (ability to detect as low viral load as 2 copies/ul; See FIGS. 1A-2F, 2A-2H) by amplifying long amplicons derived from targets spread across the genome which are then detected directly without requiring any modification or label attached to the detected DNA. In some instances, the processes of the disclosure amplify the target nucleic acid sequence by using a multiplex set of primers configured to amplify greater than 1%, greater than 5%, greater than 10%, greater than 20%, greater than 30%, greater than 40%, greater than 50%, greater than 60%, greater than 70%, or greater than 80% of a genome encoding the target nucleic acid sequence. Since the platforms of the disclosure are directly sequencing the amplicons (as opposed to detecting a fluorescence from such amplicons), there is no theoretical limit as to how many different regions of a target specimen may be simultaneously amplified to generate amplicons—the technique disclosed herein is not limited by detection of a fluorescence signal. These advantages allow the sensitivity of the disclosed assay for the target nucleic acid to be two copies of the target nucleic acid per microliter. Further, the accuracy of the assay for the target nucleic acid is higher than 99% as compared to the accuracy of a PCR assay.

Other Definitions

Unless defined otherwise, all technical and scientific terms used herein have the same meaning as commonly understood by one of ordinary skill in the art to which this invention belongs. For purposes of interpreting this specification, the following definitions will apply and whenever appropriate, terms used in the singular will also include the plural and vice versa.

As used herein the term "Ct" or "ct" refers to "cycle threshold" and is defined as the number of cycles required for a fluorescent signal to cross the threshold (i.e. exceeds background level). Ct levels are inversely proportional to the amount of target nucleic acid in the sample (i.e. the lower the Ct level the greater the amount of target nucleic acid in the sample). In a real time PCR assay a positive reaction is detected by accumulation of a fluorescent signal. The real time assays generally undergo 40 cycles of amplification. Cts<29 are strong positive reactions indicative of abundant target nucleic acid in the sample. Cts of 30-37 are positive reactions indicative of moderate amounts of target nucleic acid Cts of 38-40 are weak reactions indicative of minimal amounts of target nucleic acid which could represent an infection state or environmental contamination.

As used herein the term, specimen (interchangeably used with the term microorganim) refers to a biological entity (e.g., a virus, a bacterium, an yeast, a flagella, or another multi-cellular organism) comprising a nucleic acid sequence. Pathogenic specimens can injure a subject, e.g., by competing with it for metabolic resources, destroying its cells or tissues, or by secreting toxins. Salubrious specimens are favorable or promote health or well-being of a subject. Examples of classes of pathogenic microorganisms include viruses, bacteria, mycobacteria, fungi, protozoa, and some helminths. Many pathogenic microorganisms are further subdivided into serotypes, which can differentiate strains by their surface and antigenic properties. Examples of salubrious microorganisms include probiotics, such as *Lactobacillus paracasei* Shirota.

As used herein the terms "infectious", "virulent" or "virulence" are used interchangeably and refer to a microorganism's ability to infect or damage a host by causing disease. The pathogenicity of an organism, its ability to cause disease, is determined by its virulence factors. Virulence factors are molecules produced by bacteria, viruses, fungi, and protozoa that add to their effectiveness and enable them to achieve for example: colonization of a niche in the host, including attachment to cells; immunoevasion, evasion of the host's immune response; immunosuppression; inhibition of the host's immune response entry into and exit out of cells (if the pathogen is an intracellular one); or to obtain nutrition from the host. Specific pathogens possess a wide array of virulence factors. Some are chromosomally encoded and intrinsic to a bacteria (e.g. capsules and endotoxin), whereas others are obtained from mobile genetic elements like plasmids and bacteriophages (e.g. some exotoxins). Virulence factors encoded on mobile genetic elements can spread through horizontal gene transfer, and can convert harmless bacteria into dangerous pathogens. For instance, bacteria like *Escherichia coli* O157:H7 gain the majority of their virulence from mobile genetic elements. Gram-negative bacteria secrete a variety of virulence factors at host-pathogen interface, via membrane vesicle trafficking as bacterial outer membrane vesicles for invasion, nutrition and other cell-cell communications.

As used herein the term "genomic surveillance" refers to a systematic collection, analysis, and interpretation of nucleic acid sequencing data from a sample. For geotagging or geotracking the sample, a geographic position information is assigned to each sample at time of collection. In preferred embodiments, the nucleic acid sequencing data is obtained with pore sequencing methods or sequencing-by-synthesis methods. The systematic collection considers data from, for example, nucleic acid variations detected with geotracking as a specimen "spreads" from one location to another such as single nucleotide polymorphisms (SNP's), restriction fragment length polymorphisms (RFLP's), short tandem repeats (STRs), variable number of tandem repeats (VNTR's), hypervariable regions, mini satellites, dinucleotide repeats, trinucleotide repeats, tetranucleotide repeats, simple sequence repeats, indels, insertion elements to systematically monitor changes in the nucleic acid sequences associated with a sample.

As used herein the term "wild type" is a term of the art understood by skilled persons and means the typical form of an organism, strain, gene or characteristic as it occurs in nature as distinguished from mutant or variant forms. As used herein the term "variant" should be taken to mean the exhibition of qualities that have a pattern that deviates from what occurs in nature. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.).

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. Sequence homologies may be generated by any of a number of computer programs known in the art, for example BLAST or FASTA, etc. A suitable computer program for carrying out such an alignment is the GCG Wisconsin Bestfit package (University of Wisconsin. U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60).

Percent homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software that may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

The terms "nucleic acid", "polynucleotide", "nucleotide", "nucleotide sequence", and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

As used herein the term "amino acid" includes natural and/or unnatural or synthetic amino acids, including glycine and both the D or L optical isomers, and amino acid analogs and peptidomimetics.

As used herein the term "sample", generally refers to any source of nucleic acids—either from an specimen, from a subject "hosting" the specimen or both—that can be informative of an environment. It may refer to samples derived from a subject, such as a nasal swab, blood, plasma, urine, tissue, faces, bone marrow, saliva, cerebrospinal fluid, or any other suitable tissue sample. It may refer to swab samples that are collected from surfaces in food processing facilities, long-term care facilities, hospitals, restaurants, or any suitable surface comprising nucleic acids. It may refer to a sample that comprises a biological tissue, soil, water, air, air filter materials, animal production, feed, manure, crop production, manufacturing plants, or any other suitable samples. Such samples may be derived from a hospital or a clinic and they may be analyzed on a mobile platform.

As used herein, the term "subject," can refer to a human or to another animal. An animal can be a mouse, a rat, a guinea pig, a dog, a cat, a horse, a rabbit, and various other animals. A subject can be of any age, for example, a subject can be an infant, a toddler, a child, a pre-adolescent, an adolescent, an adult, or an elderly individual.

Nucleic Acid Sequence Data Generation and Analysis Report by a Fully Automated Sequencing Platform Systems, methods and devices are provided for characterizing biomolecules, for example by monitoring electrical parameters as they pass through a pore, such as a nanopore under an applied electric field are known in the art. See for example, WO2013016486, describing Nanopore sensor for biomolecular characterization. Numerous other techniques for sequencing biomolecules are also available, such as Sanger sequencing, synthetic sequencing, pyrosequencing, sequencing by hybridization, massively parallel gene bead clone sequencing, and non-enzymatic real-time single molecule sequencing. WO2010080617, for instance, discusses techniques for characterizing methylation levels, including methods such as immunoprecipitation, digestion with methyl sensitive enzymes, methylation sensitive PCR, and DNA methylation binding columns. WO1996029593, for example, discusses characterization of polymer molecules based on interactions at monomer interfaces. Such systems generally measure the passage and/or electrical parameter of biomolecules in and around the nanopores, especially when the biomolecules pass through or interact with the nanopores. Improvements of such systems, provide systems and methods that can better control the electrical properties in and around the nanopore, to allow the characterization of a wide variety of biomolecules, including different forms of biomolecules, if desired. Alternatively, sequencing-by-synthesis platforms have been well described by Illumina, Ion Torrent, Genia, and others. These alternative platforms can also be used to collect sequencing data for use with the methods disclosed herein.

In preferred embodiments the sequencing comprises contacting the amplicons with a transmembrane pore such that at least one strand of the amplicons of the target nucleic acid moves through the pore. In such instances, one or more measurements can be taken as at least one strand of the amplicon of the target nucleic acid moves through the pore wherein at least one measurement is indicative of a length of the amplicon of the target nucleic acid generated during the amplification of the target specimen. As previously discussed, taking of the one or more measurements detects a direct signal from the at least one strand of the amplicon or another nucleic acid from the target including a direct signal from sub-genomic RNA (sgRNA), genomic RNA (gRNA), or a plasmid, or another nucleic acid sequence from the target that has not been subject to amplification.

Also disclosed herein are systems for analyzing and displaying high volume data analytics from fully-automated, next-generation sequencing platforms. Preferably, the sequencing platform is a pore sequencing platform or a sequencing-by-synthesis platform. Such systems can be used for simultaneous diagnosis and genomic surveillance of a multitude of microorganisms. The systems and processes disclosed herein provide for a complex multivariate analysis of nucleic acid sequencing data, which can for instance, categorizes specimens as virulent or non-virulent based on a length of the amplicons that are either detected by membranes containing nanopores (e.g., in the case of pore sequencing), or reconstructed from sequencing by synthesis methods (e.g., Illumina), or detected with other conventional sequencing methods. In some instances, the plurality of nucleic acids is treated with a reagent, such as a photosensitive dye, that binds and sequesters cell free nucleic acids prior to preparing the library or prior to sequencing the sample. This effectively removes cell free nucleic acids and some fragment nucleic acids from the analysis and can provide a cleaner sequencing signal.

Specimens

All of the functionalities described in connection with the process for distinguishing infectious from non-infectious specimens in a sample and the process for tracking an infectious disease in a population by geotagging of a target specimen are intended to be applicable to additional target specimens described herein except where the nucleic acid sequence of the target specimen is incompatible for detection by sequencing. The present disclosure contemplates detection of at least one target specimen from a plurality of nucleic acids from a sample. The sample can comprise a mixture of viral nucleic acids, mammalian nucleic acids, and bacterial nucleic acids. The sample can be geotagged for contact tracing analysis. The specimen can be detected with pore sequencing or sequencing-by-synthesis methods.

In a preferred embodiment, the process of the disclosed are used for the detection of SARS-CoV-2 and for distinguishing infectious from non-infectious signals from a SARS-CoV-2 specimen. In other preferred embodiments, the process distinguishes a panel of target specimens, such as specimens that may cause diseases with similar symptoms. In some cases, at least one specimen in the plurality of nucleic acids is selected from the group consisting of SARS-CoV-2, influenza A, influenza B, Human Respiratory Syncytial Virus (RSV). In other cases, at least one specimen in the plurality of nucleic acids is selected from the group consisting of SARS-CoV-2, influenza A, influenza B, Human Respiratory Syncytial Virus (RSV), adenovirus, coronavirus 229E, coronavirus HKU1, coronavirus NL63, human metapneumovirus, human rhinovirus/enterovirus, parainfluenza virus 1, parainfluenza virus 2, parainfluenza virus 3, parainfluenza virus 4, *Bordetella parapertussis, Bordetella pertussis, Chlamydophila pneumoniae, Mycoplasma pneumoniae*. In yet other cases, the panel is a food safety panel, and the disclosure distinguishes at least one specimen from the *Escherichia* genus, the *Listeria* genus, the *Salmonella* genus, or the *Campylobacter* genus.

Some families of microorganisms comprise both harmless and highly pathogenic microorganisms. The *Escherichia* family of pathogens, for example, comprise lethal and harmless strains of *E. coli*. Thus it is not only relevant to be able to identify a microorganism in a sample, but it is also relevant to be able to characterize it as being a potentially pathogenic sequence or a salubrious sequence. The processes described herein, can be used for example, to identify SARS-CoV-2 specimens that are intact and capable of causing infection. In other aspects, the disclosure provides a large multi-variate analysis of nucleic acid sequencing data that identifies variants that can also be associated with higher pathogenicity or virulence in microorganisms of the Coronavirus genus, microorganisms of the *Salmonella* genus, microorganisms of the *Campylobacter* genus, microorganisms of the *Listeria* genus, microorganisms of the *Campylobacter* genus and microorganisms of the *Escherichia* genus.

Non-limiting examples of specimens from the Corona genus that can be distinguished with the methods of the disclosure include both viruses with low case fatality rate (CFR, HCoV-NL63, HCoV-229E, HCoV-OC43, and HCoV-HKU1, and those with high CFR, namely, MERS-CoV, SARS-CoV, and SARS-CoV-2. Non-limiting examples of microorganism of the *Salmonella* genus include *Salmonella Enteritidis, Salmonella Typhimurium, Salmonella* Newport, *Salmonella* Javiana, *Salmonella Infantis, Salmonella* Montevideo, *Salmonella Heidelberg, Salmonella* Muenchen, *Salmonella* Saintpaul, *Salmonella* Oranienburg, *Salmonella* Braenderup, *Salmonella* Paratyphi B var. L(+) Tartrate+, *Salmonella* Agona, *Salmonella* Thompson, and *Salmonella* Kentucky. Non-limiting examples of microorganism of the *Escherichia* genus include *E. coli* 0103, *E. coli* 0111, *E. coli* 0121, *E. coli* 0145, *E. coli* 026, *E. coli* 045, and *E. coli* 0157. Non-limiting examples of *Listeria* species include *monocytogenes, grayii, weishimeri, marthii, innocua, ivanovii, seeligeri*. Non-limiting examples of microorganisms of the *Campylobacter* genus include *C. jejuni, C. lari*, or *C. coli*.

In yet other embodiments, the disclosure contemplates applying the process disclosed herein to the detection of sexually transmitted disorders (STDs). Sexually transmitted infections (STIs), also referred to as sexually transmitted diseases (STDs), are infections that are commonly spread by sexual activity, especially vaginal intercourse, anal sex and oral sex. However, STIs can also be transmitted by non-sexual contact with donor tissue, blood, breastfeeding, or during childbirth, which may result in poor outcomes for the infant. Some STIs can cause infertility. One Of the challenges in monitoring STIs is that many viruses and bacteria that cause infectious diseases often do not cause symptoms in their initial phases, which results in a greater risk of a subject passing the disease on to others. More than 30 different bacteria, viruses, and parasites can be transmitted through sexual activity. Bacterial STIs include *Chlamydia*, gonorrhea, and syphilis. Viral STIs include genital herpes, HIV/AIDS, and genital warts. Parasitic STIs include trichomoniasis. In some instances, the disclosure contemplates detection of a specimen that is associated with a sexually transmitted disease. In some instances, the specimen is selected from the group consisting of bacterial vaginosis, *Chlamydia*, gonorrhea, genital herpes, hepatitis, HIV/AIDS, human papillomavirus (HPV), pelvic inflammatory disease (PID), syphilis, trichomoniasis, and other STDs. Non-limiting examples of sexually transmitted infections where the processes of the disclosure can be applied include *Chlamydia*, gonorrhea, Hepatitis B virus (HBV), *Herpes simplex* virus type 2 (HSV-2), Human immunodeficiency virus (HIV), Human papillomavirus (HPV), Syphilis, Trichomoniasis, *Mycoplasma genitalium*, Urinary Tract infections and wound infections. Non-limiting examples of pathogens causing those infections include *Chlamydia trachomatis, Neisseria gonorrhoeae*, Hepatitis B virus (HBV), *Herpes simplex* virus type 2 (HSV-2), Human immunodeficiency virus (HIV), Human papillomavirus (HPV), *Treponema pallidum, Trichomonas vaginalis, Mycoplasma genitalium, Acinetobacter baumannii, Citrobacter freundii, Enterobacter aerogenes, Enterobacter cloacae, Escherichia coli, Klebsiella oxytoca, Klebsiella pneumoniae, Morganella morganii, Proteus mirabilis, Proteus vulgaris, Providencia stuartii, Pseudomonas aeruginosa, Enterococcus faecalis, Enterococcus faecium, Staphylococcus saprophyticus, Staphylococcus agalactiae, Aspergillus flavus, Candida albicans, Candida dubiniensis, Candida glabrata, Candida parasilosis, Candida tropicalis, Trichosporon asahii, Trichosporon beigelii, Acinetobacter baumannii, Citrobacter freundii, Enterobacter aerogenes, Enterobacter cloacae, Escherichia coli, Klebsiella oxytoca, Klebsiella pneumoniae, Morganella morganii, Proteus mirabilis, Proteus vulgaris, Pseudomonas aeruginosa, Enterococcus faecalis, Enterococcus faecium, Staphylococcus agalactia, Staphylococcus aureus Staphylococcus saprophyticus, Candida albicans, Candida glabrata, Candida parapsilosis, Candida dubliniensis*, or *Candida tropicalis.*

Contact Tracing

Whether naturally occurring or intentionally inflicted, pathogenic specimens can cause illness, disability, and death in individuals while disrupting entire populations, economies, and governments. First, quantitative information is essential for risk assessments because some pathogens are naturally present in environments and their infectious doses vary vastly. Second, large-scale, robust, and rapid genomic sequencing of samples enables an unbiased characterization of nucleic acid sequences being analyzed that may allow the identification of a broader range of distinct microorganisms from a sample. Third, sequencing of samples supports monitoring of important changes in the genomic sequences of specimens (variant detection) as it continues to circulate and evolve. Such variant analysis can provide crucial information to advance public health research, for instance it can inform areas of transmission dynamics, host response, and evolution of a microorganism. Last, but not least, the processes of the disclosure can help distinguish fragmented sequences that are unlikely to cause an infection, from highly contagious sequences.

In some aspects, provided herein is a process for tracking an infectious disease in a population by geotagging comprising: (a) receiving a sample, wherein the sample comprises a plurality of nucleic acids and adding a geotag to the sample by providing geographic position information of the sample to a server by a computer so that the server creates a location based geotag based on the geographic position information of the sample; (b) sequencing the plurality of nucleic acids in the sample and creating sequencing digital data having one or more nucleic acid digital sequences derived from a microorganism in the sample; (c) transmitting the sequencing digital data to the server; (d) associating the geographic position information of the sample with the sequencing digital data transmitted to the server; and (e) tracking the infectious disease by associating the one or more nucleic acid sequences derived from the microorganism with the geographic position information of the sample.

In some instances, the sample is derived from a location and a geotag is associated with the sample. The location can be a food processing facility, a healthcare facility, a learning center (e.g., schools, daycares), a penitentiary, an commuter station (e.g., an airport, a train station, a bus station), an entertainment center (e.g., a movie theater, a bar), or a place of worship (e.g., a church, a mosque, a temple). The sample can be from a sub-location within the location and the sublocation can have its own geotag. The geotag can be a digital number associated with a file or a molecular barcode added to the sample prior to sequencing. The sub-location can be any part of the location, such as a room or an area within the location, including a machine, a portal entry, or an equipment within the location.

In specific embodiments the disclosure contemplates global monitoring of an outbreak of a disease cause by any one of the specimens disclosed herein. In such instances, the disclosure contemplates monitoring the global levels of a specimen from a location that concentrates multiple difference sources of samples. In such cases, the location is a sewage water stream.

In specific embodiments, the sample is derived from a subject of any age. When derived from a subject, the sample can be a nasal swab, a blood sample, a plasma samples, a saliva sample, or a stool sample, of the subject.

Data Analysis and Classification of Specimens

The raw sequence data collected from the sequencing reaction includes a large complex multivariate data set that includes a plurality of sequences found in the sample, as well as the quality read at each base. From this large complex data set, the following parameters are extracted:

(a) Read quality: The raw sequences include information on the quality of the sequences per base. The quality scores can be used in a Bayesian model where classifications are statistically sensitive to these quality scores. Furthermore the quality scores can reveal more on possible relations that content of samples have with the accuracy of sequencing platform. The read quality data can indicate a length of a sequencing read.

(b) Sequence time: The raw sequences also include information on the time when the sequence was read by the sequencer. The number of sequences form the same source as a function of time can reveal a lot more information than we currently have. In addition, these time data, can be useful in generating reports for all or some of the samples earlier than it is currently done.

(c) Trimmed portions of sequences: During demultiplexing of the sequences initial and terminal portions of those sequences are trimmed. Those portions include adapters, index barcodes, and primers. The main data extracted from the trimmed portions, identifies which sample the sequence belonged to. This decision however is influenced by sequencing errors, and special properties of the involved sequences. The information on accuracy of this decision, and other factors is lost with trimming. Moreover the quality of these portions can be used as an indicator for the quality of the entire sequence.

(d) Clustering: An important step in the pipeline involves clustering sequences that are close enough to each other and representing all the sequences within a cluster by a consensus sequence. This reduces the data significantly and make is easier to classify these sequences. However these differences, even if minute, carry information that gets lost with clustering. Clustering with more stringent criteria, or no clustering can lead into higher resolution and perhaps finer classification.

In some cases, machine learning can be employed to consider variant sequences in the samples, in addition to a length of a detected amplicon. In such instances, samples comprising a specimen with a known pathogenesis, e.g., samples comprising SARS-CoV-2 nucleic acid sequences, can be labeled as "COVID-19 samples" in a training set. Samples associated with SARS-CoV-2 active infections can be labeled "virulent." Samples that are not associated with an active infection, but that are positive for SARS-CoV-2 can be labeled "non-virulent." A length of an amplicon can be used to determine if the variant sequences are originating from a fragment source or an intact source (viable). For machine learning purposes, samples associated with "symptomatic" pathogenesis can be labeled "symptomatic." Samples associated with "asymptomatic" pathogenesis can be labeled "asymptomatic." The system can then be instructed to identify patterns that are clearly distinct between "asymptomatic", "symptomatic", "virulent", and "non-virulent", while the length of the amplicons is used to determine the integrity of the source.

In unsupervised learning, the data has no labels. The machine algorithm looks for whatever patterns it can find. This can be interesting if, for instance, every sample analyzed is from a sample that is positive for a SARS-CoV-2 nucleic acid sequence. It could, for example, be used for characterization and surveillance of nucleic acid strains that have greater virulence. With the methods of the disclosure, the system can be instructed to only consider sequencing data from amplicons of a certain size, an approach that eliminates from review the analysis of non-fragmented sources.

The systems provided herein can be used for finding patterns in datasets comprising sequences from a plurality of distinct microorganisms. Microorganisms live in many distinct ecological niches on the planet and have inhabited the earth for many hundreds of millions of years. Indeed, microorganisms may be the most abundant life form by mass, and they are highly adaptable to external forces. The vast majority of microorganisms are essential to human, animal, and plant life. Occasionally, however, a microorganism is classified as a pathogen because it may cause an acute infectious disease or trigger a pathway to other chronic diseases. These microorganisms, which include viruses, bacteria, and protozoa can cause respiratory, food, air, and waterborne illnesses. The detection, quantification, and classification of such microorganisms are important when assessing health risks associated with food, air, water, or physical locations, including hospitals, schools, food processing facilities, and nursing homes. In some instances, the systems provided herein provide for the quantification of a particular microorganism in a sample comprising nucleic acid sequences from a plurality of different microorganisms.

A computer system is programmed or otherwise configured to process and transmit a data set from a mobile vehicle that is optionally certified as a CLIA lab. The computer system includes a central processing unit (CPU, also"processor" and "computer processor" herein), which can be a single core or multi core processor, or a plurality of processors for parallel processing. The computer system also includes memory or memory location (e.g., random-access memory, read-only memory, flash memory), electronic storage unit (e.g., hard disk), communication interface (e.g., network adapter) for communicating with one or more other systems, such as for instance transmitting a data set associated with said sequencing reads, and peripheral devices, such as cache, other memory, data storage and/or electronic display adapters. The memory, storage unit, interface, and peripheral devices are in communication with the CPU through a communication bus (solid lines), such as a motherboard. The storage unit can be a data storage unit (or data repository) for storing data. For instance, in some cases, the data storage unit can store a plurality of sequencing reads and provide a library of sequences associated with one or more strains from one or more microorganisms associated with a sample. The sample can be associated with a food processing facility, a diagnostic laboratory, or any other facility.

The computer system can be operatively coupled to a computer network ("network") with the aid of the communication interface. The network can be the Internet, an internet and/or extranet, or an intranet and/or extranet that is in communication with the Internet. The network in some cases is a telecommunication and/or data network. The network can include one or more computer servers, which can enable distributed computing, such as cloud computing. The network, in some cases with the aid of the computer system, can implement a peer-to-peer network, which may enable devices coupled to the computer system to behave as a client or a server.

A machine learning algorithm can be used to associate any number of nucleic acid sequence reads with a presence of microorganism in a sample. Similarly, a machine learning algorithm may be able to associate any number of sequencing reads with a virulence of a microorganism. Computer-implemented methods for generating a machine learning-based classifier in a system may require a number of input datasets in order for the classifier to produce highly accurate predictions. Depending on the microorganism, matrix, and the microorganisms abundance in the real life samples of the matrix, the data can be in range of 100, 1000, 10000, 100000, 1000000, 10000000, 100000000 sequencing reads. A machine learning algorithm is selected from the group consisting of: a support vector machine (SVM), a Naive Bayes classification, a random forest, Logistic regression and a neural network.

Systems, Software Media, Networks, and Methods for Displaying a Report

Provided herein are systems, software media, networks, kits, and methods for performing computer analysis on sequencing data of a sample. The analysis can extract information from virulent sequence reads and non-virulent sequence reads, compare both types of information, and identify sequence variants based on probabilistic modeling and statistical inference. The analysis may include distinguishing between SARS-CoV-2 variants, *E. coli* variants, *Salmonella* variants, *Listeria* variants, *Campylobacter* variants, and variants of other microorganisms.

In various disclosed systems, software media and methods disclosed herein, identifying a putative variant can comprise comparing the genomic sequences to sequences of a bank of sequences from one or more previously analyzed samples. Scoring a putative variant can comprise adjusting a probability based on a machine learning method trained with sets of virulent sequences or and non-virulent sequences. Identifying and scoring a putative variant can comprise making an inference at a chromosomal locus. For example, at least four groups of pathogenic *Escherichia coli* have been identified: a) Enterotoxigenic *Escherichia coli* (ETEC), b) Enteropathogenic *Escherichia coli* (EPEC), c) Enterohemorrhagic *Escherichia coli* (EHEC), and Enteroinvasive *Escherichia coli* (EIEC). While ETEC is generally associated with traveler's diarrhea some members of the EHEC group, such as *E. coli* O157:H7, can cause bloody diarrhea, blood-clotting problems, kidney failure, and death. Thus, it is important to be able not only to identify individual microorganism, but also to distinguish putative variants amongst them at the genomic level. Similarly, many discrepancies have been reported regarding the mortality of SARS-CoV-2. Being able to distinguish putative variants amongst the existing SARS-CoV-2 strains may provide a viable strategy for the management of pathogenic outbreaks.

In various applications, making an inference can comprise using one or more of the following: a probabilistic model, a statistical inference, a Bayesian inference, and a Bayesian network model. In some designs, making an inference can be based on one or more of the following: a prior probability of finding virulent and non-virulent variants (e.g., disease causing versus non-disease causing variants) a set of sequence reads aligned across the chromosomal locus, an error rate of the high-throughput sequencing instrument, aa process model of the rate of mutation of a microorganisms, a call at the chromosomal locus derived from one or more other samples, prior knowledge of a common polymorphism at the chromosomal locus in one or more reference samples, prior knowledge of one or more recurrent cancer variants at a location (e.g., a hospital, a food processing facility, a school, or any other location), a percentage of virulent cells in a sample containing a pathogenic microorganims, describing a variant by a probabilistic model, describing a set of aligned sequence reads across the chromosomal locus by a probabilistic model, and describing a percentage of disease causing microorganims in a sample by a probabilistic model.

In some instances, an error rate can be provided in quality validation for a base call. A pathogen containing sample can comprise one or more microorganism that can cause disease. A percentage used herein can be described by a binary variable. Thus, in some aspects, provided herein are systems and methods that allow the quantitation of disease causing microorganism in a sample.

In some aspects, provided herein is a system for generating and displaying a graphical user interface for high volume data analytics (see FIG. 5), the system comprising: at least one processor operatively connected to a memory, the at least one processor when executing, is configured to: receive nucleic acid sequencing metrics; analyze and group the nucleic acid sequencing metrics into a pathogenic demographic hierarchy; determine summary information for the nucleic acid sequencing metrics in each level of the pathogenic demographic hierarchy; and generate a navigable user interface display comprising: at least one selectable drawer associated with the summary information for the nucleic acid sequencing metrics, wherein the at least one selectable drawer includes a display of a title of a respective pathogenic demographic hierarchy; and wherein the at least one selectable drawer is associated with a respective summary view of the summary information for the nucleic acid sequencing metrics.

EXAMPLES

Figure 1B:
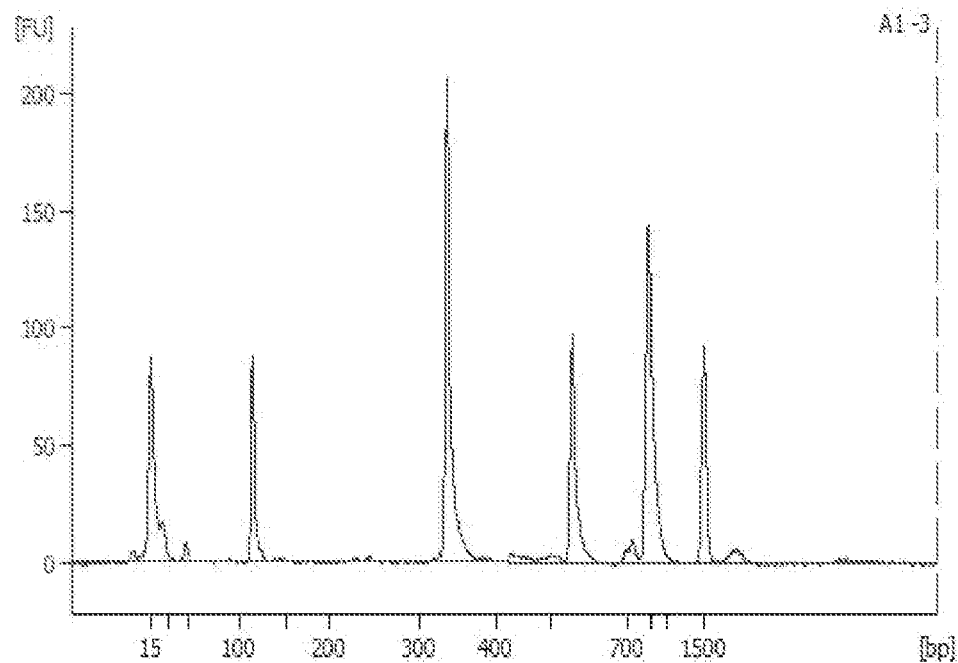
FIG. 1B (FIG. 1B), FIG. 1C (FIG. 1C), FIG. 1D (FIG. 1D), FIG. 1E (FIG. 1E), FIG. 1F (FIG. 1F), collectively, demonstrate that specimens with low viral load (equivalent to Ct of ~38) can still have amplicons for all fragments and that nucleic acid extraction does not necessarily cause the fragmentation. Each panel illustrates the output of an RNA quality assay with serial dilutions (FIG. 1B=1000 copies/ul.

Example 1: Establishing the Limit of Detection of a Process of the Disclosure with a Synthetic SARS-CoV-2 Nucleic Acid Sequence A synthetic nucleic acid sequence encoding SARS-CoV-2 was received from Twist Biosciences. After a reverse transcription (RT) step converting the RNA to complementary DNA (cDNA), amplicons were generated from this synthetic nucleic acid template in a multiplex PCR utilizing a set of multiplex primers that bind to different locations on the 'N' gene of SARS-CoV-2 to produce different length amplicons. FIG. 1A is a diagram illustrating the strategy for amplification and validating the process disclosed herein. FIG. 1A discloses a schematic for amplification that is expected to produce 100 bp, 300 bp, 500 bp, and 800 bp fragments from intact templates. FIG. 1B (FIG. 1B), FIG. 1C (FIG. 1C), FIG. 1D (FIG. 1D), FIG. 1E (FIG. 1E), FIG. 1F (FIG. 1F) (collectively, FIGS. 1B-1F) depict the results of an RNA quality assay with serial dilutions of the synthetic RNA in order to establish a lower limit of detection for the methodology.

Figure 1C:
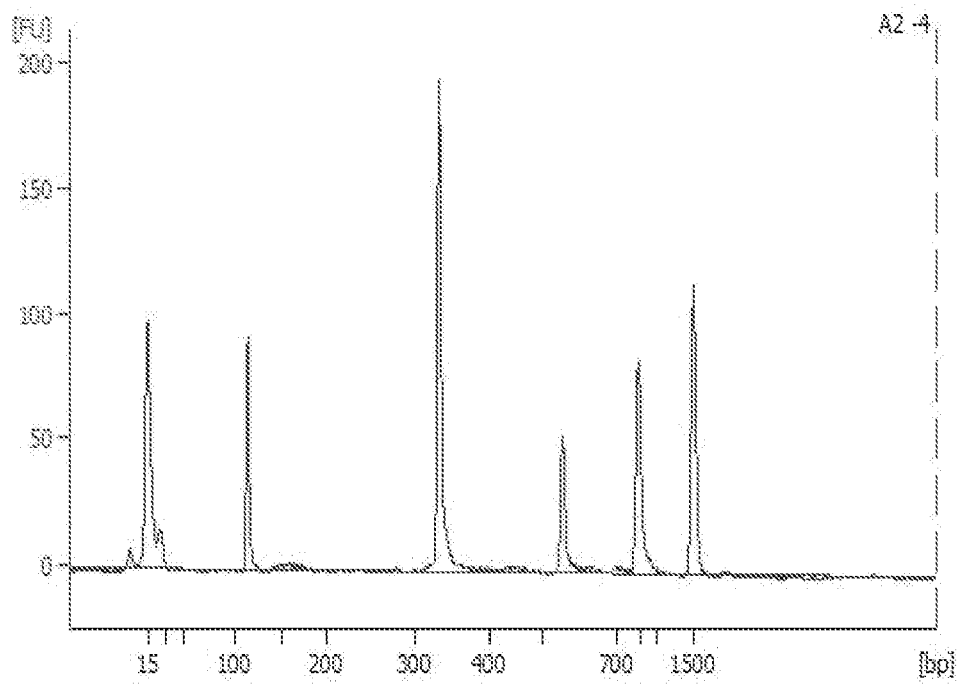
FIG. 1C=100 copies/ul.
Figure 1D:
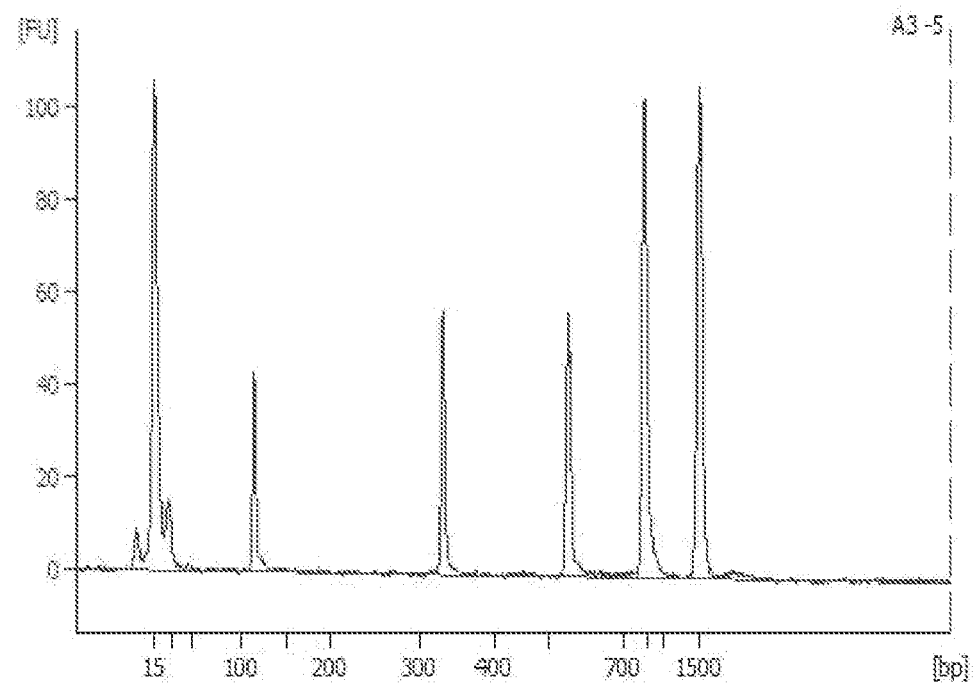
FIG. 1D=10 copies/ul.
Figure 1E:
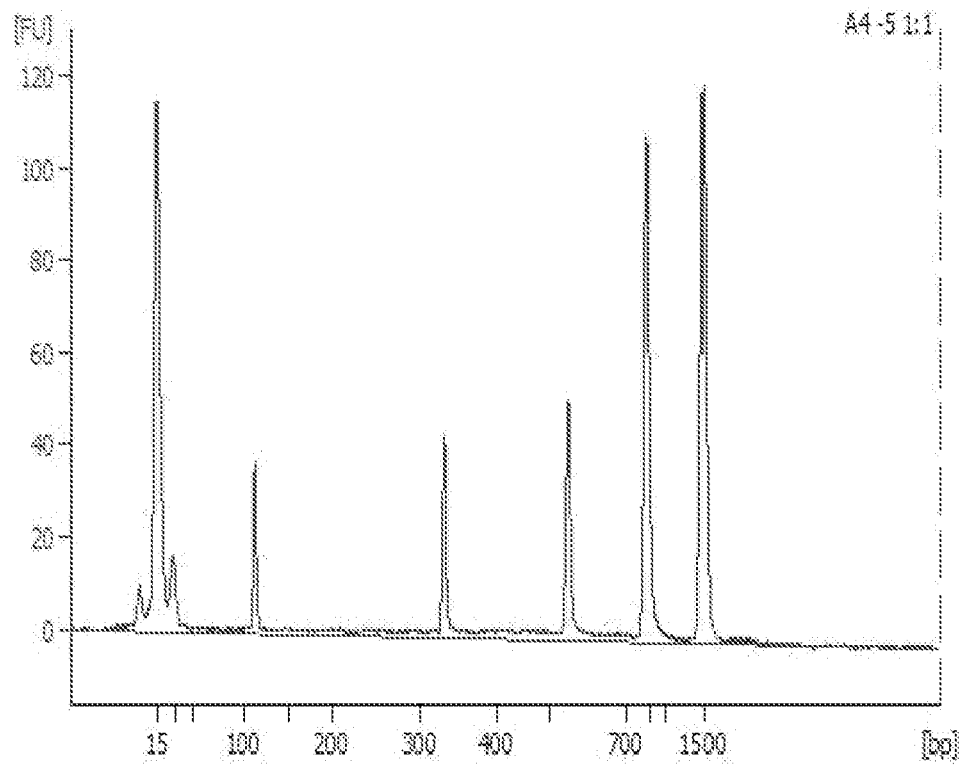
FIG. 1E=5 copies/ul.
Figure 1F:
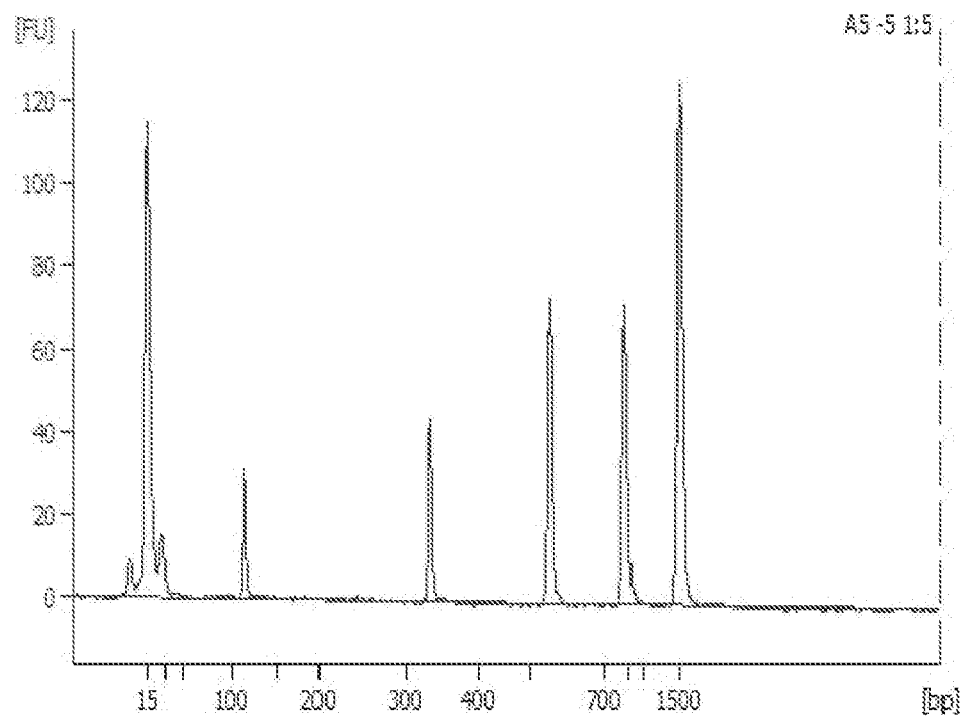
FIG. 1F=2 copies/ul) of synthetic viral RNA generated by Twist Biosciences.

The amplicons generated from the the SARS-CoV-2 synthetic nucleic acid template were run on an Agilent DNA 1000 bioanalyzer gel. FIGS. 1B-1F indicate that with the decrease in RNA concentration, the process detected a decrease in concentration of the respective fragments (as expected), but the methodology also detected presence of longer fragments. The data demonstrate that specimens with low viral load (equivalent to Ct of ~38) can still have amplicons for all fragments and that nucleic acid extraction does not necessarily cause the fragmentation. Each panel in FIGS. 1B-1F illustrates the output of an RNA quality assay with serial dilutions (FIG. 1B=1000 copies/ul; FIG. 1C=100 copies/ul; FIG. 1D=10 copies/ul; FIG. 1E=5 copies/ul; and FIG. 1F=2 copies/ul) of synthetic viral RNA. Tables 1 through 5 demonstrate the limit of detection of the assay.

TABLE 1

1000 copies/ul

| Size [bp] | Conc. [ng/µl] | Molarity [nmol/L] |
|---|---|---|
| 15 | 4.2 | 424.2 |
| 114 | 3.54 | 47 |
| 333 | 7.43 | 33.8 |
| 556 | 3.19 | 8.7 |
| 831 | 5.64 | 10.3 |
| 1,500 | 2.1 | 2.1 |

TABLE 2

100 copies/ul

| Size [bp] | Conc. [ng/µl] | Molarity [nmol/l] |
|---|---|---|
| 15 | 4.2 | 424.2 |
| 114 | 1.85 | 24.7 |
| 332 | 3.83 | 17.5 |
| 551 | 2.51 | 6.9 |
| 830 | 2.21 | 4 |
| 1,500 | 2.1 | 2.1 |

TABLE 3

10 copies/ul

| Size [bp] | Conc. [ng/µl] | Molarity [nmol/l] |
|---|---|---|
| 15 | 4.2 | 424.2 |
| 114 | 1.23 | 16.5 |
| 332 | 1.17 | 5.3 |
| 553 | 1.1 | 3 |
| 830 | 2.53 | 4.6 |
| 1,500 | 2.1 | 2.1 |

TABLE 4

5 copies/ul

| Size [bp] | Conc. [ng/µl] | Molarity [nmol/l] |
|---|---|---|
| 15 | 4.2 | 424.2 |
| 113 | 0.87 | 11.7 |
| 330 | 0.74 | 3.4 |
| 548 | 0.89 | 2.5 |
| 834 | 2.26 | 4.1 |
| 1,500 | 2.1 | 2.1 |

TABLE 5

2 copies/ul

| Size [bp] | Conc. [ng/µl] | Molarity [nmol/l] |
|---|---|---|
| 15 | 4.2 | 424.2 |
| 114 | 0.67 | 9 |
| 332 | 0.69 | 3.1 |
| 551 | 1.19 | 3.3 |
| 830 | 1.35 | 2.5 |
| 1,500 | 2.1 | 2.1 |

Example 2: Extraction and Analysis of Serial Dilutions of a Real-World Specimen with Low Ct In this experiment, a real-world specimen with low Ct (~25) was diluted serially in a background of a negative clinical specimen and all the dilutions were extracted through KingFisher automated extraction and the extracted RNA were processed through Clear Dx™ Clear Dx™ SARS-CoV-2 Test is a multiplexed RT-PCR and next-generation DNA sequencing (NGS) in vitro diagnostic test on the Oxford Nanopore GridION Sequencer intended for the qualitative detection of SARS-CoV-2 viral RNA in human nasopharyngeal swab, oropharyngeal swab, anterior nasal swab, mid-turbinate swab, nasopharyngeal wash/aspirate, nasal aspirate, and bronchoalveolar lavage specimens from individuals suspected of COVID-19 by their healthcare provider. Testing is limited to laboratories that are certified under the Clinical Laboratory Improvement Amendments of 1988 (CLIA), 42 U.S.C. § 263a, to perform high complexity tests.

The Clear Dx™ system (see U.S. Pat. No. 10,597,714B2, entitled automated priming and library loading device) uses a Hamilton STAR robotic platform for automation of liquid handling and includes all the required ancillary equipment, such as thermocyclers, barcode reader, and magnet block, needed for the test. The system also houses the GridION nanopore sequencer developed by Oxford Nanopore Technologies (ONT).

RNA Extraction:

The Clear Dx™ SARS-CoV-2 Test started with RNA (in elution buffer), manually extracted from respiratory specimens, using MagMAX Viral RNA Isolation Kit (catalog #AM1939) through the manual workflow as recommended by the manufacturer.

Assay & Bioinformatics Workflow:

The automated Clear Dx™ SARS-CoV-2 Test synthesized cDNA from extracted RNA for each of the samples loaded into the well plates in independent reverse transcription reactions. Then the viral target amplicons were captured from the synthesized cDNA through a multiplex PCR process using a panel of barcoded target capture primers. After this "Target-capture" PCR step, a Solid Phase Reversible Immobilization (SPRI) bead-based cleanup was performed during which all the excess primers and any short amplification products were removed. Following this, the amplicons were subject to another round of PCR, termed as "Barcoding PCR", where a second set of barcodes were added to the amplicons using the rapid library primers from ONT. Following this step, the dual barcoded amplicons from all the samples were pooled together and cleaned up through another SPRI bead process. After this step, the ONT sequencing adapters are ligated to all the barcoded amplicons and then sequenced on the GridION sequencer. In this experiment, a real-world specimen with low Ct (~25) was diluted serially in a background of a negative clinical specimen and all the dilutions were extracted through KingFisher automated extraction and the extracted RNA were processed through Clear Dx'.

Our bioinformatics pipeline, Clear Dx™ BIP (version Dv5.0) performed a series of steps including demultiplexing, error correction and alignments on the sequencing reads of the amplicons to make the detection calls. The SARS-CoV-2 detection algorithm takes the relative ratios of the sequencing signal for SARS-CoV-2 primers, the internal PCR control, and the human housekeeping gene into account to make an invalid/positive/negative call. Samples with insufficient total read coverage were classified as invalid. The remaining samples have their SARS-CoV-2 signal compared to empirically derived thresholds, and here the thresholds included a length of the detected amplicon. These thresholds distinguish true SARS-CoV-2 signal from noise, as well as from fragmented sources of SARS-CoV-2, which are unlikely to be infectious. Each primer has its own threshold and the pipeline leverages the redundancy of SARS-CoV-2 specific primers to make a call.

TABLE 12

Extraction and Clear Dx assay of serial dilutions of subject samples with low Ct

| Dilution factor | N1 Ct | N2 Ct | No. of target amplicons with detectable reads (N = 30) | % SARS CoV-2 coverage |
|---|---|---|---|---|
| 1× | 24.5 | 24.9 | 20.97 ± 0.04 | 51.9% |
| 10× | 28.9 | 29.6 | 18.53 ± 4.63 | 45.9% |
| 100× | 32.6 | 33.7 | 16.4 ± 2.27 | 40.6% |
| 300× | 34 | 35.6 | 10.69 ± 3.08 | 26.5% |
| 900× | 35.4 | 36.5 | 4.87 ± 2.36 | 12.1% |
| 1200× | 38.4 | 38.6 | 4.35 ± 2.31 | 10.8% |

Figure 3:
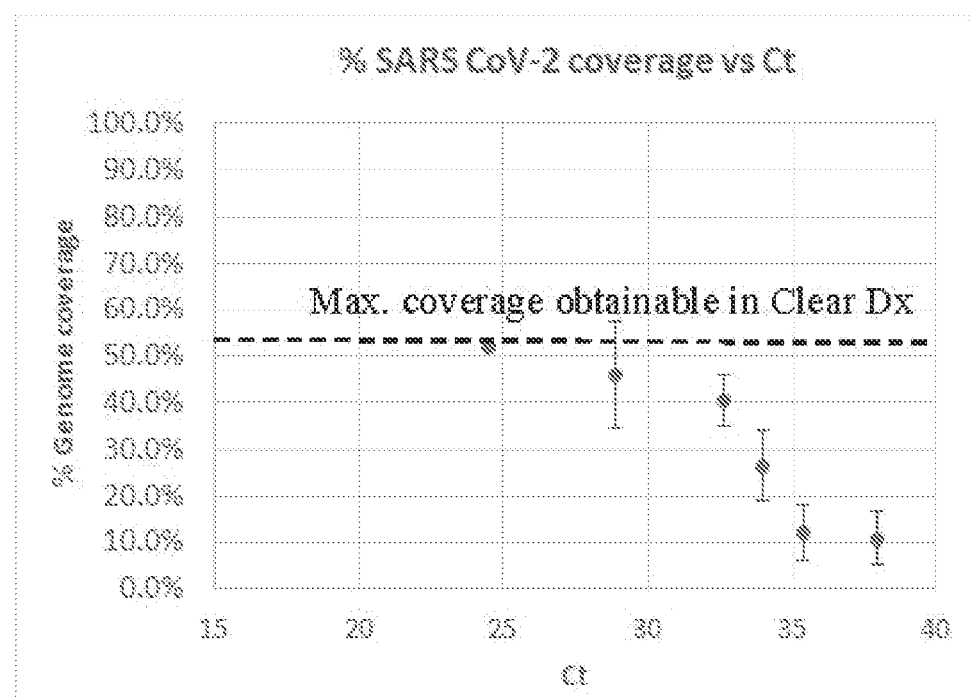
FIG. 3 (FIG. 3) contrasts detection of a target nucleic acid in samples with intact RNA and high ct as opposed to samples with high fragmentation and moderate Ct.
Figure 4A:
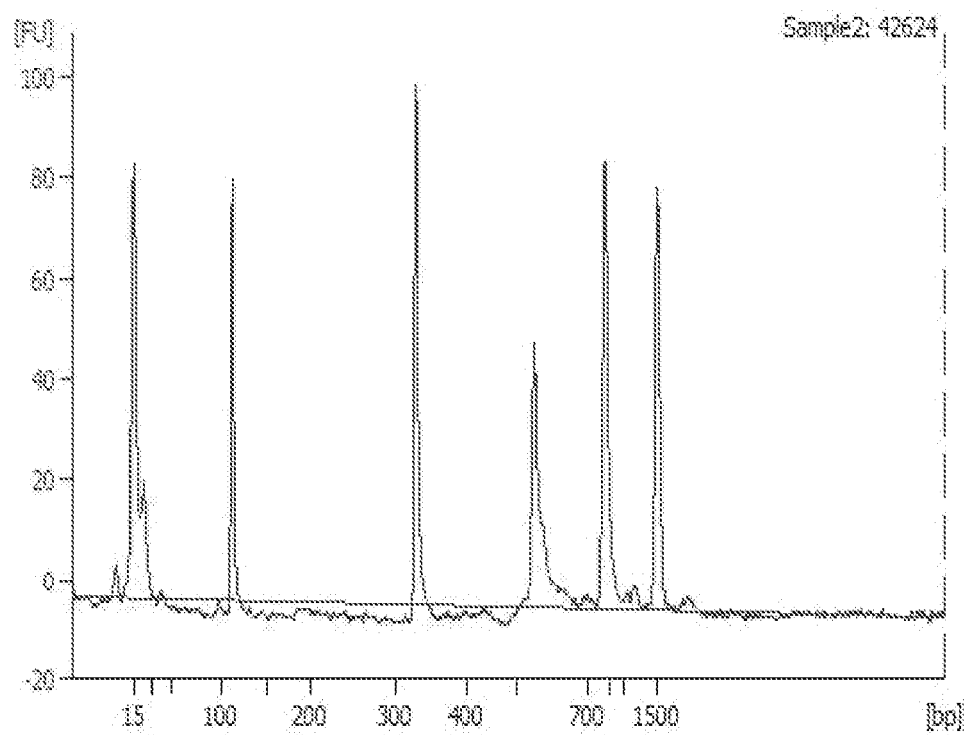
FIG. 4A through FIG. 4F (FIG. 4A-4E) illustrate detection of amplicons from a target nucleic acid from five distinct subjects amplified in a multiplex PCR and run on an Agilent DNA 1000 bioanalyzer gel.
Figure 4B:
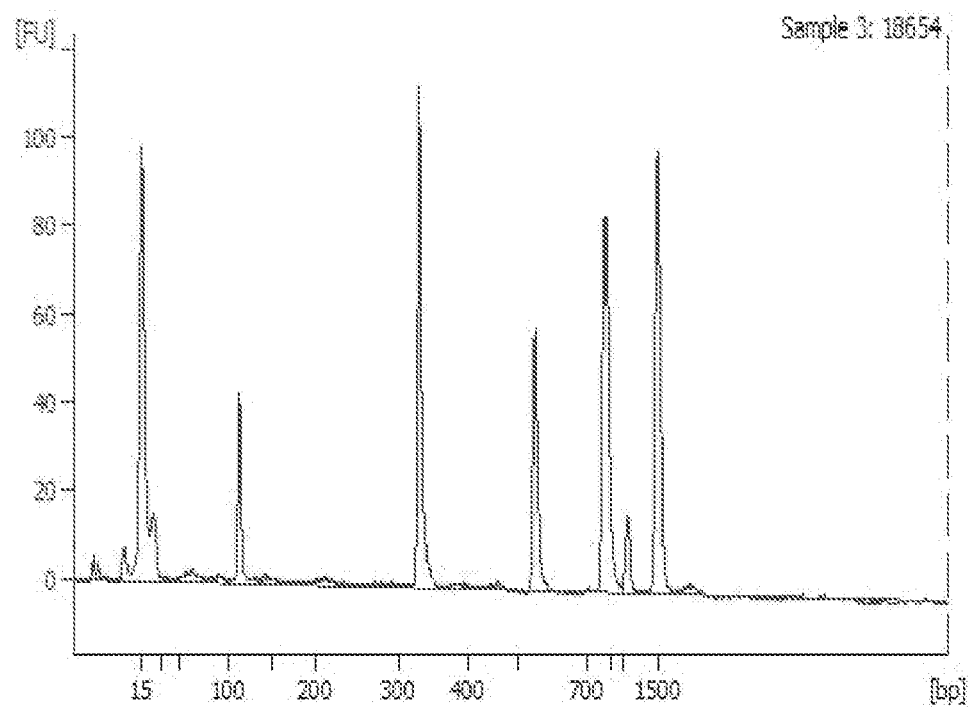
Figure 4C:
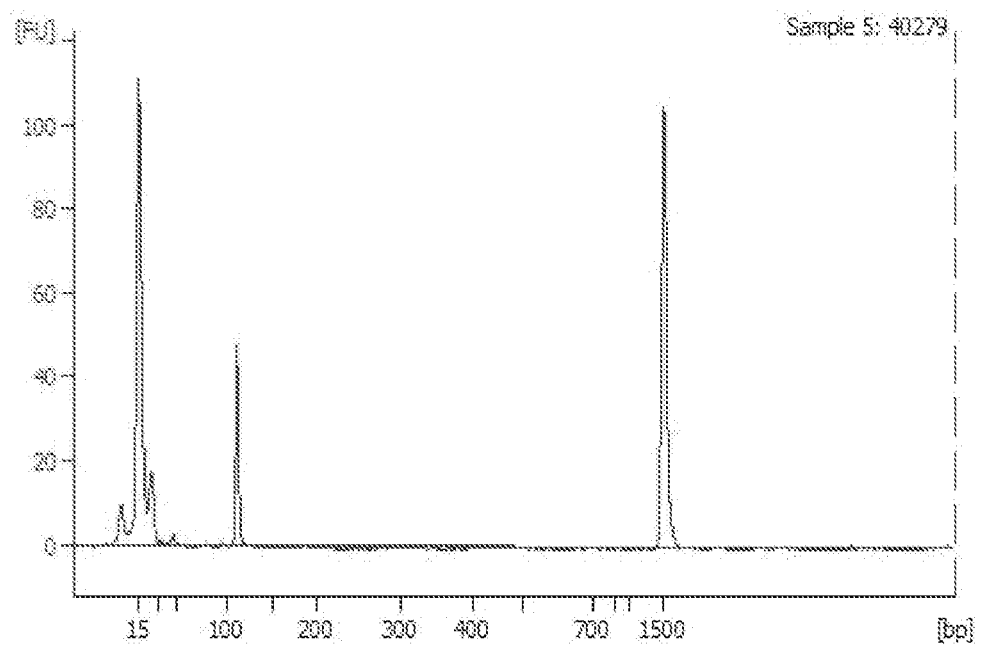
Figure 4D:
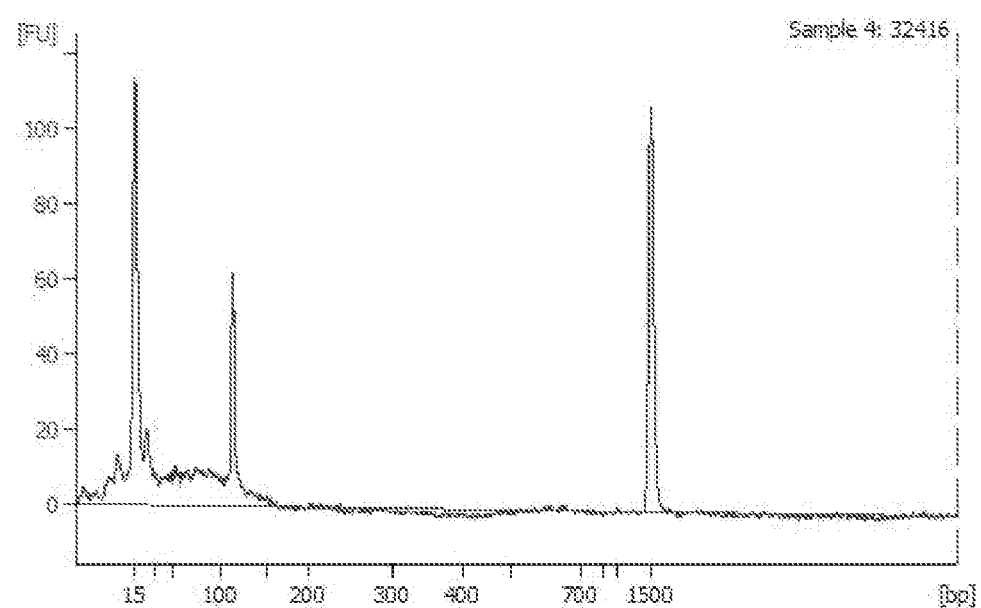
Figure 4E:
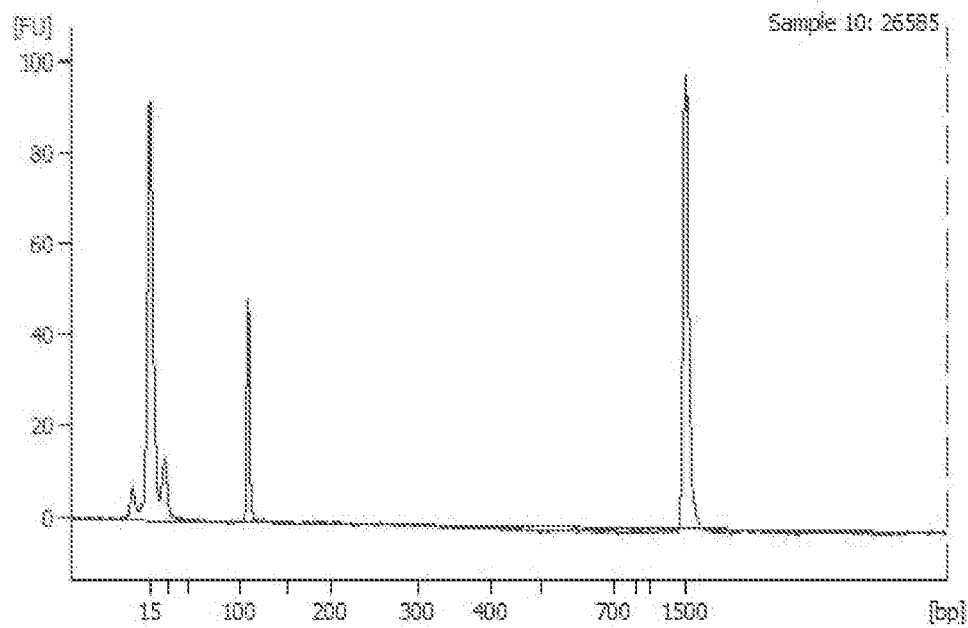
Figure 4F:
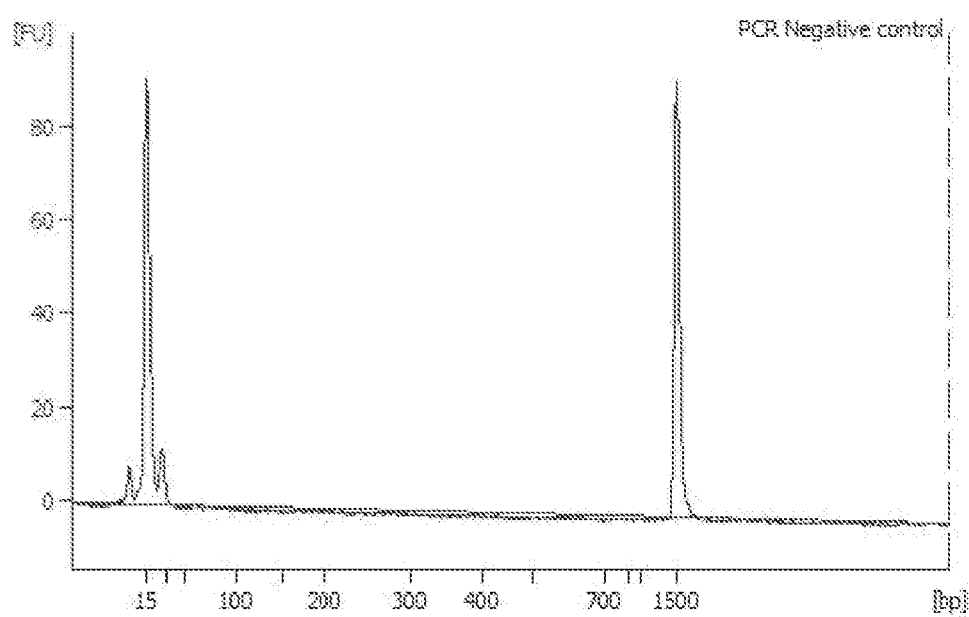
Figure 6:
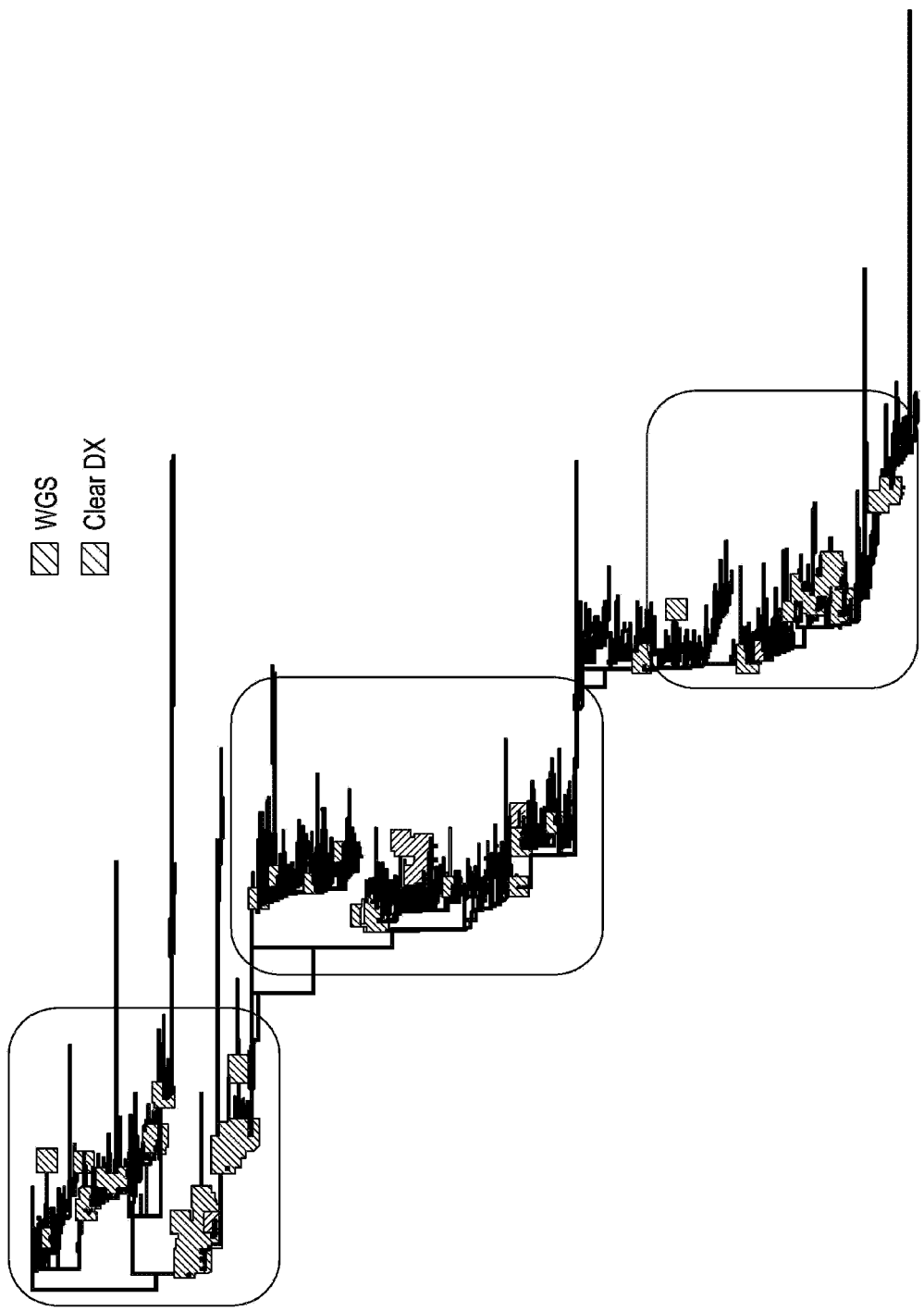
FIG. 6 (FIG. 6) illustrates that the subtyping obtained with the methods of the disclosure aligns with the classification obtained by WGS.

FIG. 3 (FIG. 3) contrasts detection of a target nucleic acid in samples with intact RNA and high ct as opposed to samples with high fragmentation and moderate Ct, illustrating the significance of detection of two or more amplicons of the target nucleic acid of a length greater than 500 bases. FIG. 4A through FIG. 4F (FIG. 4A-4E) illustrate detection of amplicons from a target nucleic acid from five distinct subjects amplified in a multiplex PCR and run on an Agilent DNA 1000 bioanalyzer gel. FIG. 4F illustrate the output of the negative control. FIG. 5 (FIG. 5) illustrates a graphical user interface reporting subtype, clade, and variants detected by a process of the disclosure, in a format used for disclosure to the subject. FIG. 6 (FIG. 6) illustrates that the subtyping obtained with the methods of the disclosure aligns with the classification obtained by WGS.

Example 3: Establishing the Limit of Detection of a Process of the Disclosure with SARS-CoV-2 Nucleic Acid Sequences from Subjects SARS-CoV-2 from subjects were received from different state public health labs for analysis. In most cases, these samples were received in the form of extracted RNA preserved at the state labs at −80 C and shipped to us on dry ice. The RNA extracts from the samples are first processed through a RT step as before to produce cDNA, which was then subsequently used in a multiplex PCR. Amplicons were generated from these samples in a multiplex PCR utilizing a set of multiplex primers that bind to different locations on the 'N' gene of SARS-CoV-2 to produce different length amplicons, such as the fragments illustrated in FIG. 1A.

Figure 2A:
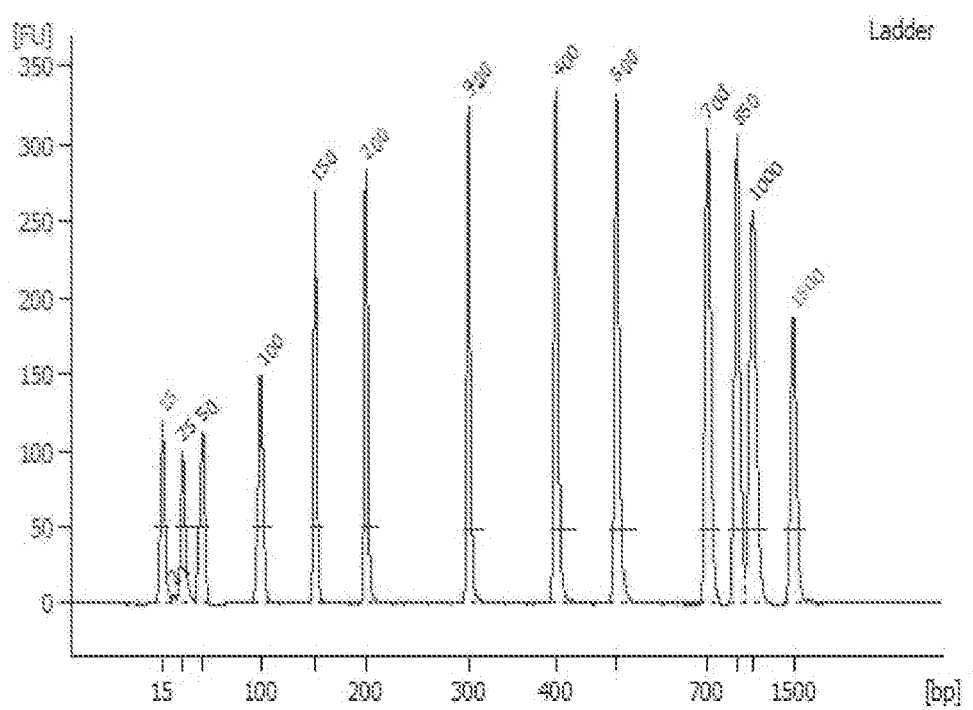
FIG. 2A through FIG. 2H (FIG. 2A-2I) illustrate detection of a target nucleic acid at low viral loads (Ct ~38) from serial dilutions of a sample. The target nucleic acid was amplified and the amplicons were analyzed on an Agilent DNA 1000 bioanalyzer gel.
Figure 2B:
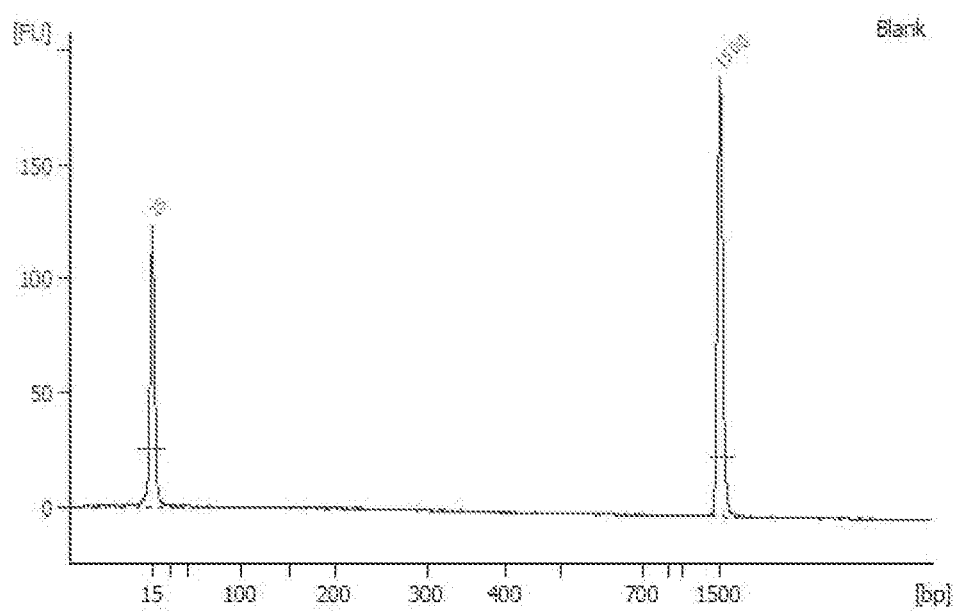
Figure 2C:
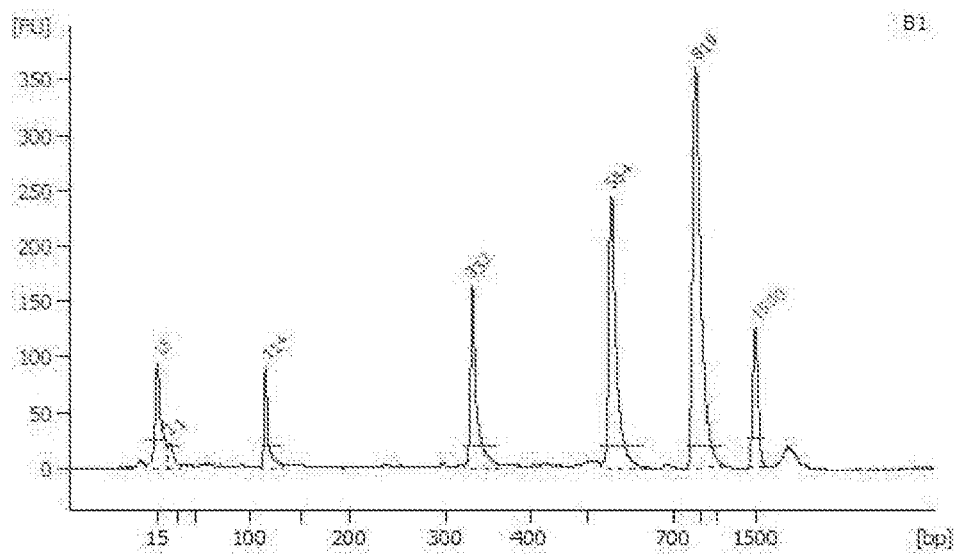
Figure 2D:
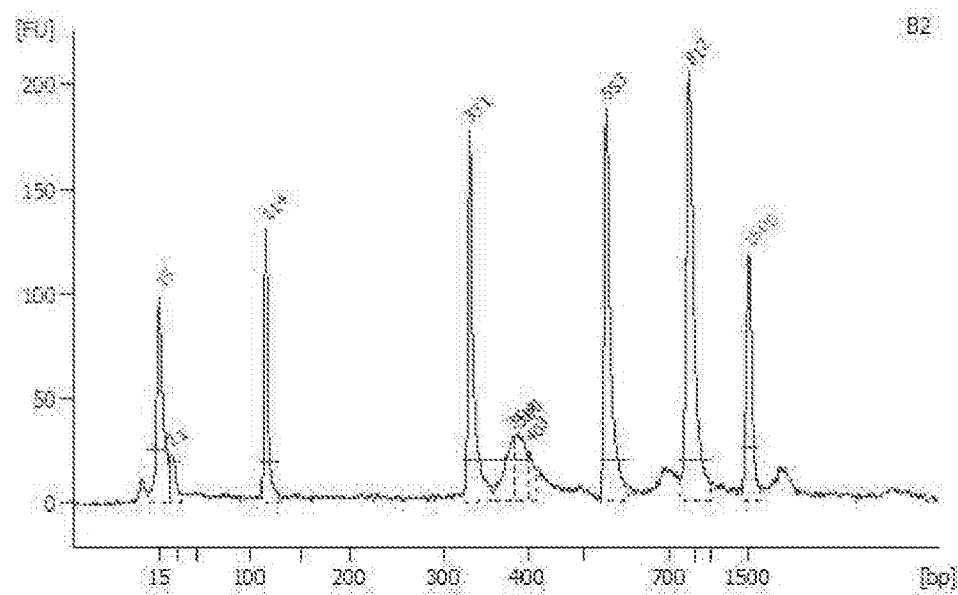
Figure 2E:
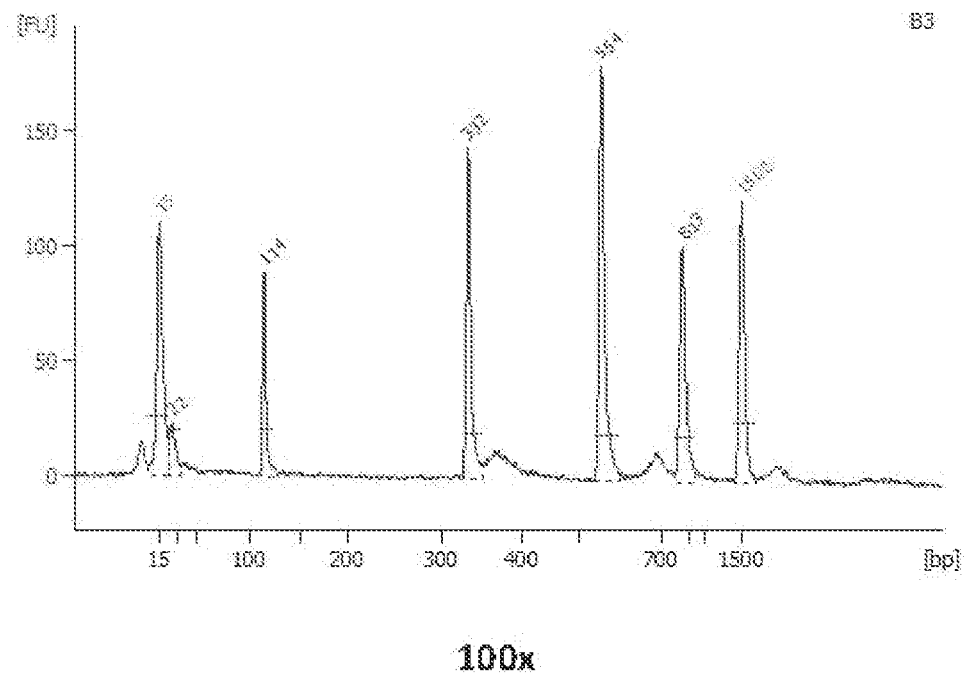
Figure 2F:
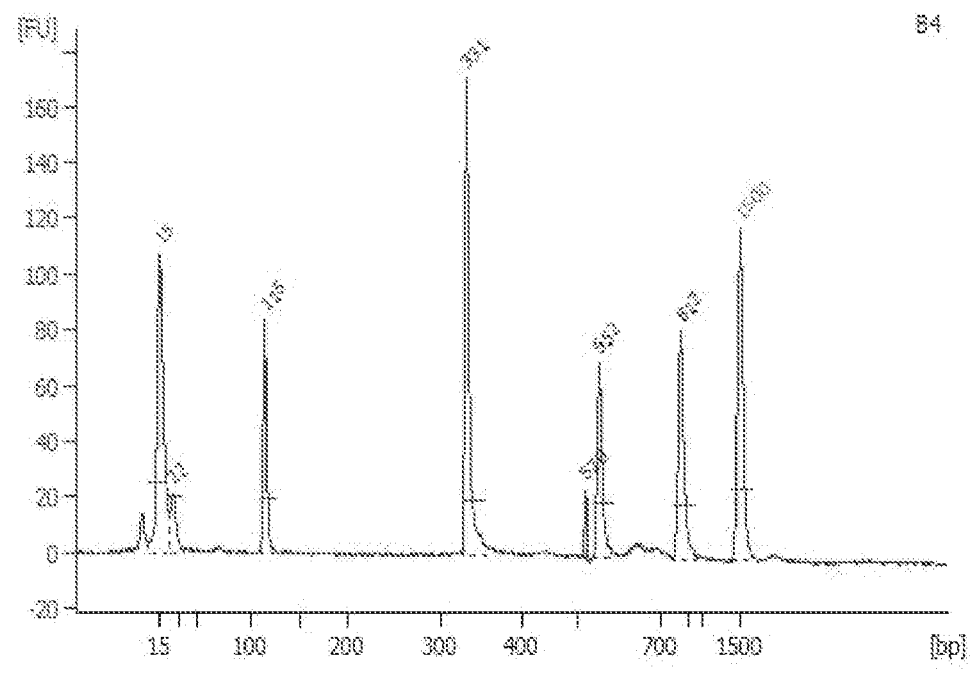
Figure 2G:
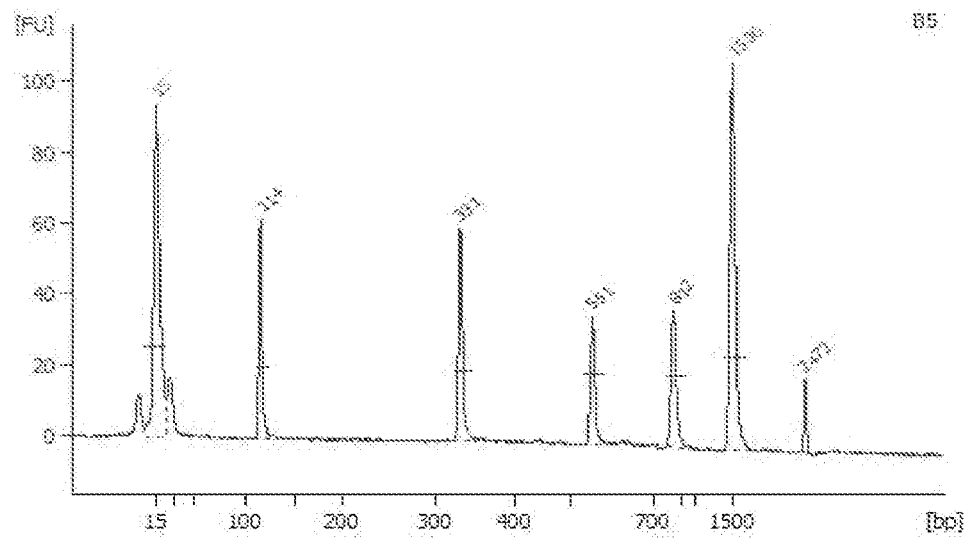
Figure 2H:
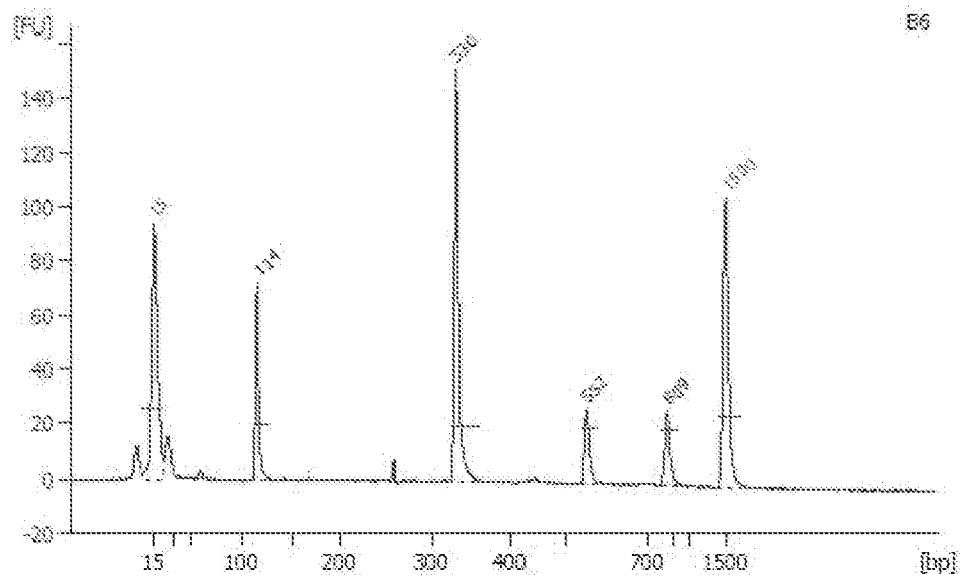

FIG. 2A through FIG. 2H (FIG. 2A-2H) illustrate detection of SARS-CoV-2 from subjects at low viral loads (Ct ~38) from serial dilutions of the samples received. The target nucleic acid was amplified and the amplicons were analyzed on an Agilent DNA 1000 bioanalyzer gel. FIG. 2A illustrate the output of the standard reference, the "ladder." FIG. 2B illustrate the output of the negative control, "blank." FIG. 2C-2H illustrate detection of as little as 1.1 nmol/l of the target nucleic acid in a specimen (FIG. 2C=1× dilution; FIG. 2D=10× dilution; FIG. 2E=100× dilution; FIG. 2F=300× dilution; FIG. 2G=900× dilution; and FIG. 1H=1200× dilution). Tables 6 through 11 demonstrate the limit of detection of the assay in these clinical samples.

TABLE 6

1× Dilution

| Size [bp] | Conc. [ng/µl] | Molarity [nmol/l] |
|---|---|---|
| 15 | 4.2 | 424.2 |
| 114 | 2.81 | 37.3 |
| 332 | 4.5 | 20.6 |
| 554 | 6.32 | 17.3 |
| 819 | 10.69 | 19.8 |
| 1,500 | 2.1 | 2.1 |

TABLE 7

10× Dilution

| Size [bp] | Conc. [ng/µl] | Molarity [nmol/l] |
|---|---|---|
| 15 | 4.2 | 424.2 |
| 114 | 3.55 | 47 |
| 331 | 4.43 | 20.3 |
| 553 | 4.31 | 11.8 |
| 812 | 5.62 | 10.5 |
| 1,500 | 2.1 | 2.1 |

TABLE 8

100× Dilution

| Size [bp] | Conc. [ng/µl] | Molarity [nmol/l] |
|---|---|---|
| 15 | 4.2 | 424.2 |
| 114 | 2.14 | 28.4 |
| 332 | 2.9 | 13.3 |
| 554 | 3.63 | 9.9 |
| 813 | 2.13 | 4 |
| 1,500 | 2.1 | 2.1 |

TABLE 9

Table 9 - 300× Dilution

| Size [bp] | Conc. [ng/µl] | Molarity [nmol/l] |
|---|---|---|
| 15 | 4.2 | 424.2 |
| 115 | 2.05 | 27.1 |
| 331 | 3.7 | 16.9 |
| 552 | 1.38 | 3.8 |
| 812 | 1.78 | 3.3 |
| 1,500 | 2.1 | 2.1 |

TABLE 10

900× Dilution

| Size [bp] | Conc. [ng/µl] | Molarity [nmol/l] |
|---|---|---|
| 15 | 4.2 | 424.2 |
| 114 | 1.63 | 21.6 |
| 331 | 1.2 | 5.5 |
| 551 | 0.7 | 1.9 |
| 812 | 0.8 | 1.5 |
| 1,500 | 2.1 | 2.1 |

TABLE 11

Table 10 - 1200× Dilution

| Size [bp] | Conc. [ng/µl] | Molarity [nmol/l] |
|---|---|---|
| 15 | 4.2 | 424.2 |
| 114 | 1.94 | 25.7 |
| 330 | 3.29 | 15.1 |
| 552 | 0.53 | 1.5 |
| 809 | 0.6 | 1.1 |
| 1,500 | 2.1 | 2.1 |

This demonstrates that specimens with low viral load (equivalent to Ct of ~38) can still have amplicons for all fragment lengths and that the extraction is not necessarily causing the fragmentation.

Example 4: Analysis of 40 NP Swab Specimens

A total of 40 NP swab specimens were cultured in standard plaque assays in triplicates for determination of viability and quantitation of the live virus in the swab specimens.

The cts of the samples as detected by RT-PCR are described below and used in analysis for comparison with the detection by Clear Dx™ SARS-CoV-2 Test outlined in Example 3.

1. High viral load sample A (Ct ~20) diluted serially to produce 9 different dilutions with different Cts (20, 23.3, 26.6, 30, 33.3, 35.6, 36.6, 37.6, 40).
2. High viral load sample B (Ct ~20) diluted serially to produce 9 different dilutions with different Cts (20, 23.3, 26.6, 30, 33.3, 35.6, 36.6, 37.6, 40).
3. 10 samples across different Ct values that are Clear Dx positive and RT-PCR positive.
4. 10 samples across different Ct values that are Clear Dx negative and RT-PCR positive.
5. 2 Negatives (both Clear Dx negative and RT-PCR negative).

Figure 7:
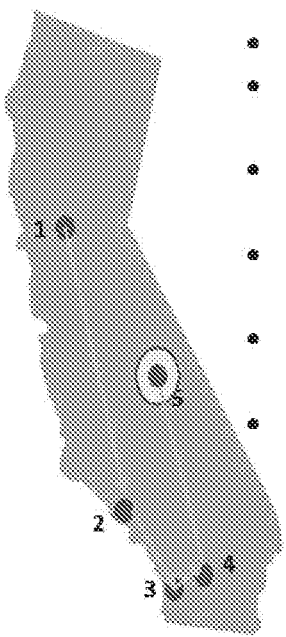
FIG. 7 (FIG. 7) illustrates a contact tracing application of the methods of the disclosure.

FIG. 7 (FIG. 7) illustrates how the results obtained with the Clear Dx™ SARS-CoV-2 Test were used for tracking the infection by associating the one or more nucleic acid sequences derived from the specimen with the geographic position information of the sample.

Example 5: Fully-Automated, Next-Generation Sequencing Platform for Simultaneous Genomic Surveillance of a Panel of Specimens Including SARS-CoV-2

Figure 8:
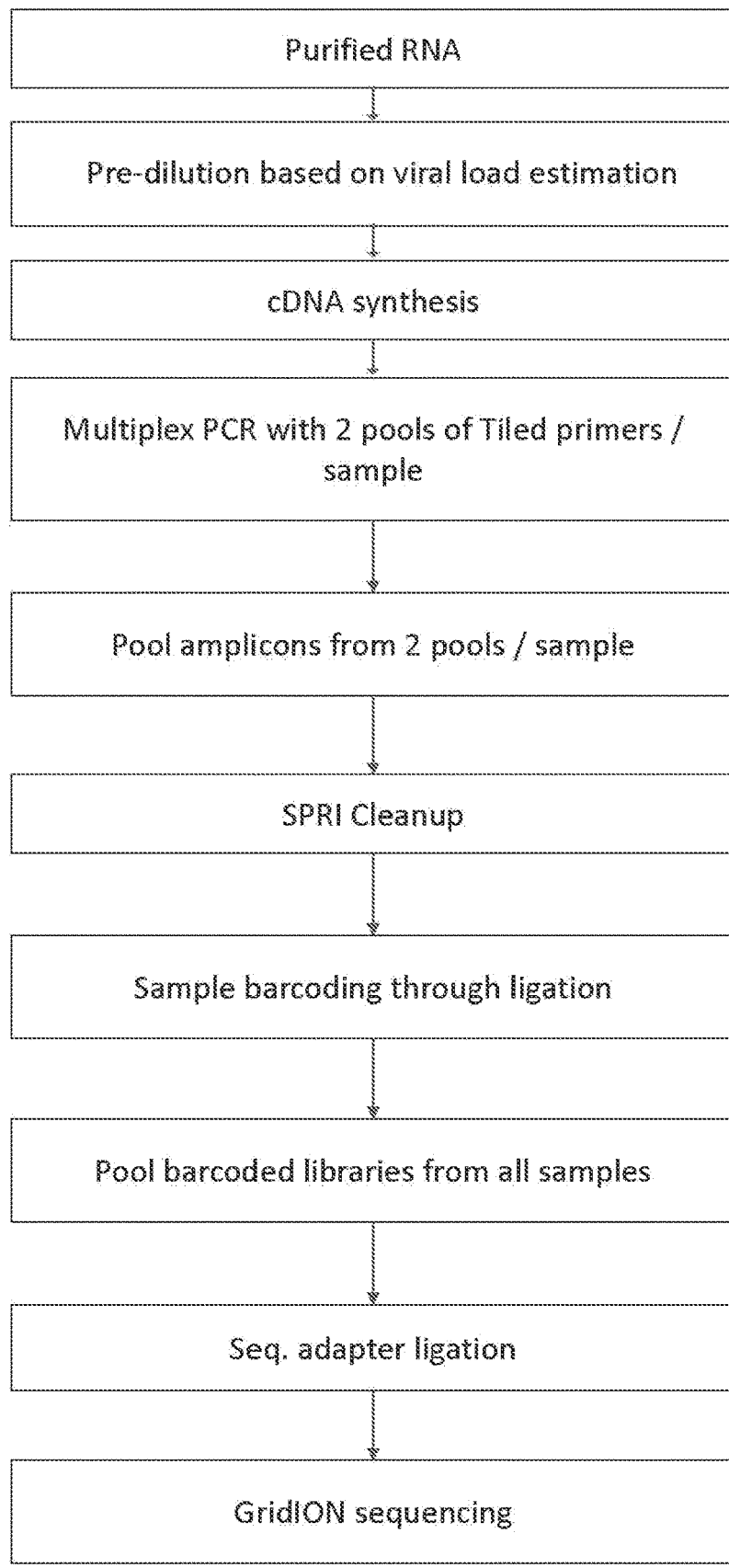
FIG. 8 (FIG. 8) is a chart outlining steps for a whole genome sequencing protocol.

FIG. 8 (FIG. 8) is a chart outlining steps for a protocol that is used for the simultaneous genomic surveillance of a panel of specimens.

Samples from subjects and locations were prepared for pore sequencing analysis on a MinION portable sequencing device manufactured by Oxford Nanopore Technologies. General techniques and protocols for pore sequencing are described by WO2010086622, entitled adaptors for nucleic acid constructions in transmembrane sequencing; WO20120164270, entitled coupling method; WO2013014451, entitled hairpin loop method for double strand polynucleotide sequencing using transmembrane pores; WO2014013260, entitled modified helicase; WO2013041878, entitled analysis of a polymer comprising polymer units; and WO2019133756, entitled Automated Priming and Library Loading Device, filed on Dec. 27, 2018.

Via sequencing multiple regions, the specimens present in the samples were detected and quantified (relative to each other). Using the aforementioned methods, raw sequencing data is generated and analyzed. Briefly, the raw data corresponds to distinctive ion current signatures from the plurality of nucleic acids present in the clinical swab sample, notably the duration and extent of current block and the variance of current levels. See WO2013041878 further describing general detection of nucleic acid sequences by pore sequencing.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are snot to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed is:

1. A process for distinguishing infectious from non-infectious microorganisms in a sample, the process comprising:
   (a) receiving the sample, wherein the sample comprises a plurality of nucleic acids from at least one microorganism;
   (b) preparing the sample for analysis by synthesizing a cDNA nucleic acid library from one or more nucleic acids from a target microorganism in the plurality of nucleic acids;
   (c) performing a nucleic acid amplification reaction with the library of step (b) with a multiplex set of primers configured to amplify a plurality of genomic regions of the target microorganism in one reaction;
   (d) sequencing the amplicons from step (c) and determining that the target microorganism in the sample is infectious when amplicons of a length greater than 500 base pairs from two or more different regions of the genome of the target microorganism are detected by sequencing, and determining that the sample is non-infectious with regard to the target microorganism when amplicons of a length greater than 500 base pairs from two or more different regions of the genome of the target microorganism are not detected.

2. The process of claim 1, wherein the detection of amplicons from 3, 4, 5, 6, 7, 8, 9, or 10 different regions of the genome of the target microorganism indicates the viability of the target microorganism in the sample.

3. The process of claim 1, wherein the length of the amplicons of the target microorganism detected in (d) is greater than 600 base pairs, greater than 650 base pairs, or greater than 700 base pairs.

4. The process of claim 1, wherein the multiplex set of primers is configured to amplify greater than 1%, greater than 5%, greater than 10%, or greater than 20% of the genome of the target microorganism.

5. The process of claim 1, wherein the sensitivity of the assay for a target nucleic acid of the target microorganism is at least 10 copies/µL, at least 50 copies/µL, at least 100 copies/µL, at least 150 copies/µL, or at least 200 copies/µL.

6. The process of claim 1, wherein the sequencing is sequencing-by-synthesis.

7. The process of claim 1, wherein the sequencing comprises contacting the amplicons with a transmembrane pore such that at least one strand of the amplicons moves through the pore.

8. The process of claim 7, further comprising taking one or more measurements as at least one strand of the amplicon moves through the pore, wherein at least one measurement is indicative of a length of the amplicon.

9. The process of claim 8, wherein the taking one or more measurements involves detecting a direct signal from at least one strand of the amplicon.

10. The process of claim 8, wherein the taking of the one or more measurements as the at least one strand of the amplicon of the target nucleic acids of the target microorganism moves through the pore is configured to detect a sub-genomic RNA (sgRNA) amplicon, a genomic RNA (gRNA) amplicon, an mRNA amplicon, a tRNA amplicon, an miRNA amplicon, or an siRNA amplicon.

11. The process of claim 1, wherein the detection of the two or more amplicons of the target nucleic acids of the target microorganism does not require detection of a fluorescent dye moiety.

12. The process of claim 1, wherein the sample is treated with a reagent that binds and sequesters cell free nucleic acids from participating in subsequent nucleic acid processing steps prior to preparing the library of step (b).

13. The process of claim 12, wherein the reagent is a photo-sensitive dye.

14. The process of claim 1, wherein sample comprises a mixture of viral nucleic acids, mammalian nucleic acids, and bacterial nucleic acids.

15. The process of claim 14, wherein at least one nucleic acid in the plurality of nucleic acids is selected from the group consisting of SARS-CoV-2, influenza A, influenza B, and Human Respiratory Syncytial Virus (RSV).

16. The process of claim 14, wherein at least one nucleic acid in the plurality of nucleic acids is selected from the group consisting of SARS-CoV-2, influenza A, influenza B, Human Respiratory Syncytial Virus (RSV), adenovirus, coronavirus 229E, coronavirus HKU1, coronavirus NL63, human metapneumovirus, human rhinovirus/enterovirus, parainfluenza virus 1, parainfluenza virus 2, parainfluenza virus 3, parainfluenza virus 4, *Bordetella parapertussis, Bordetella pertussis, Chlamydophila pneumoniae,* and *Mycoplasma pneumoniae.*

17. The process of claim 14, wherein at least one nucleic acid in the plurality of nucleic acids is from the *Escherichia* genus, the *Listeria* genus, the *Salmonella* genus, or the *Campylobacter* genus.

18. The process of claim 14, wherein at least one nucleic acid in the plurality of nucleic acids is selected from the group consisting of *Chlamydia trachomatis, Neisseria gonorrhoeae,* Hepatitis B virus (HBV), *Herpes simplex* virus type 2 (HSV-2), Human immunodeficiency virus (HIV), Human papillomavirus (HPV), *Treponema pallidum, Trichomonas vaginalis, Mycoplasma genitalium, Acinetobacter baumannii, Citrobacter freundii, Enterobacter aerogenes, Enterobacter cloacae, Escherichia coli, Klebsiella oxytoca, Klebsiella pneumoniae, Morganella morganii, Proteus mirabilis, Proteus vulgaris, Providencia stuartii, Pseudomonas aeruginosa, Enterococcus faecalis, Enterococcus faecium, Staphylococcus saprophyticus, Aspergillus flavus, Candida albicans, Candida dubiniensis, Candida glabrata, Candida parasilosis, Candida tropicalis, Trichosporon asahii, Trichosporon beigelii,* or *Staphylococcus aureus.*

19. The process of claim 1, wherein the sample is derived from a subject.

20. The process of claim 19, wherein the sample is a nasal swab, a buccal swab, a throat swab, an anal swab, a vaginal swab, a urethral/penile swab, a swab from an open wound/sore/laceration, a urine sample, a blood sample, a plasma samples, a saliva sample, or a stool sample, of the subject.

21. The process of claim 1, wherein the sample is derived from a location.

22. The process of claim 21, wherein the location is a food processing facility, a healthcare facility, aged-care facility, a learning center, a penitentiary, a commuter station, a transportation vehicle, an entertainment center, or a place of worship.

23. The process of claim 21, wherein the location is a sewage water stream.

24. The process of claim 1, wherein a barcode is added to the plurality of nucleic acids of the target microorganism in the sample in step (b) or in step (c), wherein the barcode is configured for geotracking of the sample.

25. The process of claim 1, wherein the cDNA library is prepared using a panel of target capture primers specific for amplifying a target microorganism.

26. The process of claim 1, wherein the cDNA library is prepared using a panel of random primers.

* * * * *